Figure 1:
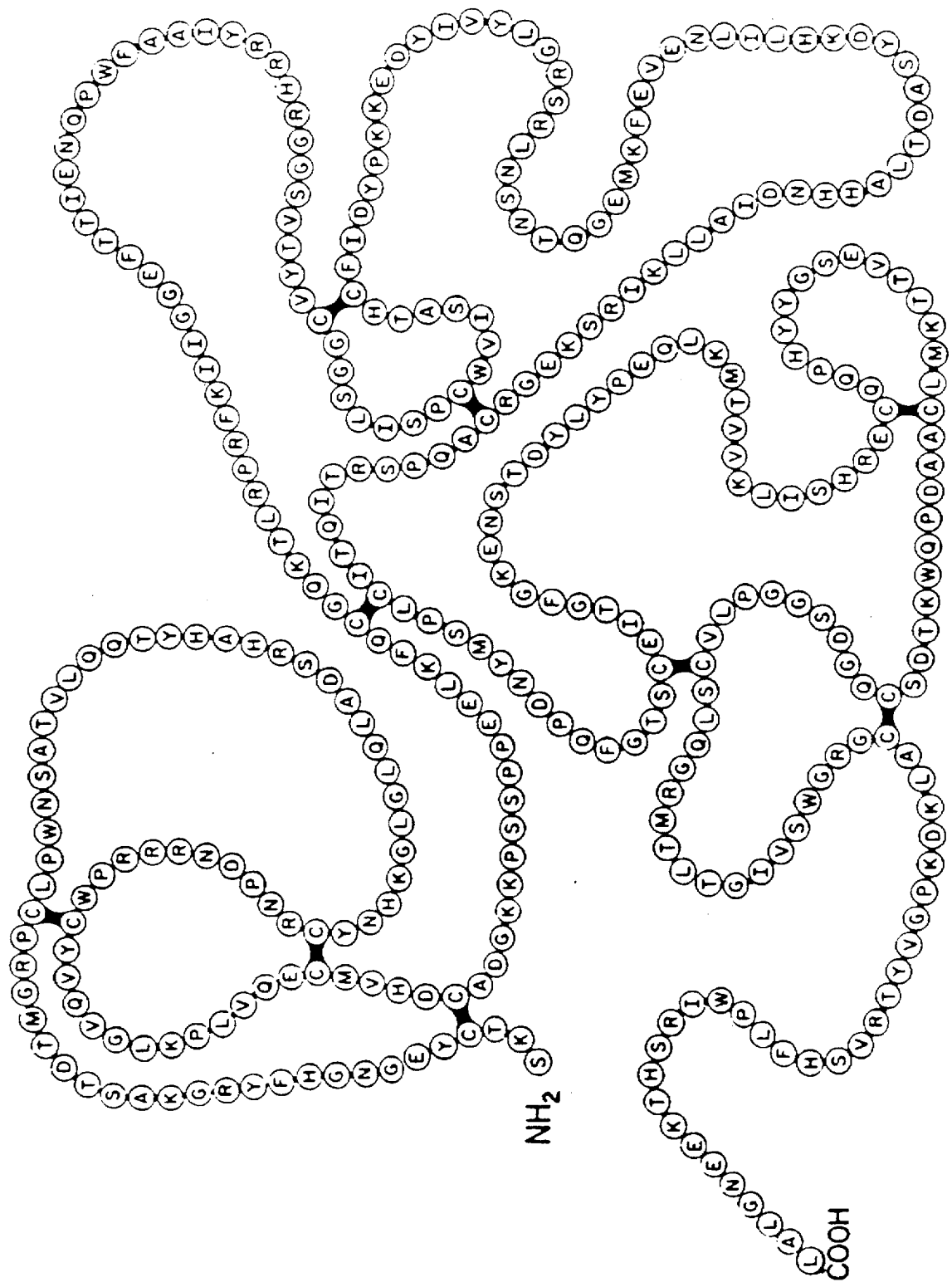

United States Patent [19]

Steffens et al.

[11] Patent Number: 5,747,291
[45] Date of Patent: May 5, 1998

[54] BIFUNCTIONAL UROKINASE VARIANTS WITH IMPROVED FIBRINOLYTIC CHARACTERISTICS AND THROMBIN INHIBITING EFFECT

[75] Inventors: Gerd J. Steffens, Aachen; Stephan Wnendt, Aachen-Forst; Johannes Schneider, Stolberg; Regina Heinzel-Wieland; Derek John Saunders, both of Aachen, all of Germany

[73] Assignee: Gruenenthal GmbH, Aachen, Germany

[21] Appl. No.: 720,012

[22] Filed: Sep. 27, 1996

Related U.S. Application Data

[62] Division of Ser. No. 93,741, Jul. 20, 1993.

[30] Foreign Application Priority Data

Jul. 15, 1993 [DE] Germany .......................... 43 23 754.1

[51] Int. Cl.$^6$ .............. C12N 9/72; C12N 15/58; C12N 15/70; A61K 38/48
[52] U.S. Cl. .............. 435/69.6; 435/69.7; 435/212; 435/320.1; 424/94.64; 536/23.2; 536/23.4
[58] Field of Search .................. 435/212, 69.6, 435/69.7, 320.1; 536/23.2, 23.4; 424/94.64

[56] References Cited

U.S. PATENT DOCUMENTS

| 4,751,180 | 6/1988 | Cousens et al. | 435/69.7 |
|---|---|---|---|
| 5,002,887 | 3/1991 | Larsen | 435/212 |
| 5,188,829 | 2/1993 | Kobayashi et al. | 424/94.63 |
| 5,256,770 | 10/1993 | Glaser et al. | 530/381 |
| 5,328,898 | 7/1994 | Greenberg | 514/12 |
| 5,376,367 | 12/1994 | Williams | 424/85.2 |
| 5,434,073 | 7/1995 | Dawson et al. | 435/216 |
| 5,571,708 | 11/1996 | Yang et al. | 435/215 |

FOREIGN PATENT DOCUMENTS

| 328957 | 8/1989 | European Pat. Off. |
|---|---|---|
| 365468 | 4/1990 | European Pat. Off. |
| 8603517 | 6/1986 | WIPO |
| WO 86/03517 | 6/1986 | WIPO |
| WO 91-01142 | 2/1991 | WIPO |
| WO 91/01142 | 2/1991 | WIPO |
| WO 91/09125 | 6/1991 | WIPO |
| 9210575 | 6/1992 | WIPO |
| WO 92/10575 | 6/1992 | WIPO |
| 9214750 | 9/1992 | WIPO |
| WO 92/14750 | 9/1992 | WIPO |
| WO 92/18139 | 10/1992 | WIPO |

OTHER PUBLICATIONS

Wun, T.C., et al., Journal of Biological Chemistry, vol. 268, "Isolation and characterization of urokinase from human plasma", pp. 3276–3283, 1982.

Steffens, et al., Hoppe–Seyler's Z. Physiol. Chem., vol. 363, "The complete amino acid sequence of low molecular mass urokinase from human urine", pp. 1043–1058, 1982.

Heyneker, H., et al., Genetics of Industrial Microorganisms, "Expression of the human urokinase gene in E. coli ", pp. 214–221, 1982.

Lijnen, H., et al., Journal of Biological Chemistry, vol. 261, "Activation of plasminogen by pro–urokinase", pp. 1253–1258, 1986.

Stump, D., et al., Journal of Biological Chemistry, vol. 261, "Urokinase–related proteins in human urine", pp. 1267–1269, 1986.

Krstenansky, J., et al., Journal of Medicinal Chemistry, vol. 30, "Anticoagulant peptides", pp. 1688–1691, 1987.

Gardell, S., et al., Journal of Biological Chemistry, vol. 264, "Isolation, characterization and cDNA cloning of a vampire bat plasminogen activator", pp. 17947–17952, 1989.

Maraganore, J., et al., Biochemistry, vol. 29, "Design and characterization of hirulogs", pp. 7095–7101, 1990.

Rydel, T., et al., Reports, "The structure of a complex of recombinant hirudin and human .alpha.–thrombin", pp. 277–280, 1990.

Thien–Kai, H., et al., Nature, vol. 353, "Domains specifying thrombin–receptor interaction", pp. 674–677, 1991.

Robinson, J., et al., TIBTECH, vol. 9, "Redesigning t-PA for improved thrombolytic therapy", pp. 86–90, 1991.

Schneider, J., Thrombosis Research, vol. 64, "Heparin and the thrombin inhibitor", pp. 677–687, 1991.

Tebbe, U. et al., Z. Kardiol. vol. 80, Supplement 3, p. 32, 1991.

Lu, H., et al., Blood, vol. 78, "Comparative thrombolytic properties of bolus injections and continuous infusions of a chimeric anticoagulant", pp. 125–131, 1991.

Collen, D., et al., Blood, vol. 78, "Basic and clinical aspects of fibrinolysis and thrombolysis", pp. 3114–2124, 1991.

Collen, D., et al., Thrombosis and Haemostasis, vol. 65, "Thrombolytic and pharmacokinetic properties of human tissue–type plasminogen activator variants", pp. 174–180, 1991.

Lijnen, H. R., et al., Thrombosis and Haemostasis, vol. 66, "Strategies for the improvement of thrombolytic agents", pp. 88–110, 1991.

Fromage, N., et al., Fibrinolysis, vol. 5, "Synthesis, purification and biological properties of a truncated mutant form of human tissue plasminogen activator produced in E. coli ", pp. 187–190, 1991.

Gruber, A., et al., Circulation, vol. 84, "Antithrombotic effects of combining activated protein C and urokinase in nonhuman primates", pp. 2454–2462, 1991.

(List continued on next page.)

*Primary Examiner*—Robert A. Wax
*Assistant Examiner*—William W. Moore, III
*Attorney, Agent, or Firm*—Evenson, McKeown, Edwards & Lenahan P.L.L.C.

[57] ABSTRACT

Bifunctional urokinase variants possessing improved fibrinolytic properties and thrombin inhibitory activities, plasmids used in the production of these polypeptides, as well as thrombolytic agents containing one of the bifunctional urokinase variants as active ingredient are described.

9 Claims, 19 Drawing Sheets

OTHER PUBLICATIONS

Eisenberg, P., Circulation, vol. 84, "Balance of procoagulant and fibrinolytic activity", pp. 2601–2603, 1991.

Vu, T.-K. H., et al., Cell, vol. 64, "Molecular cloning of a functional thrombin receptor reveals a novel proteolytic mechanism of receptor activation", pp. 1057–1068, 1991.

Flohe, R., Applied Microbiology and Biotechnology, vol. 36, "High expression vectors for the production of recombinant single-chain urinary plasminogen activator from *Escherichia coli* ", pp. 640–649, 1992.

Yao, S.-K., et al., Journal of the American Physiological Society, "Thrombin inhibition enhances tissue–type plasminogen", pp. 374–379, 1992.

Yue, S.-Y., et al., Protein Engineering, vol. 5, "Characterization of the interactions of a bifunctional inhibitor", pp. 77–83, 1992.

Szczeklik, A., et al., Arteriosclerosis and Thrombosis, vol. 12, "Persistent generation of thrombin after acute myocardial infarction", pp. 548–553, 1992.

Mellott, M., et al., Arteriosclerosis and Thrombosis, vol. 12, "Vampire bat salivary plasminogen activator", pp. 212–221, 1992.

Gunzler, W., et al., Hoppe–Seyler's Z. Physiol. Chem., vol. 363, "The primary structure of high molecular mass urokinase from human urine", pp. 1155–1165, 1992.

German abstract of DE 41 37 996, 1993.

Strube, K. H., et al., Journal of Biological Chemistry, vol. 268, "Isolation, sequence analysis and cloning of haemadin", pp. 8590–8595, 1993.

H. Thien–Khai et al., Nature, *Domains Specifying Thrombin–Receptor Interaction*, vol. 353, pp. 674–677, (Oct. 17, 1991).

T.C. Wun, et al., J. of Biol. Chem., *Isolation and Characterization of Urokinase From Human Plasma*, vol. 257, No. 6, pp. 3276–3283, (Mar. 25, 1982).

K.H. Strube, et al., J. of Biol. Chem., *Isolation, Sequence Analysis and Cloning of Haemadin*, vol. 268, No. 12, pp. 8590–8595, (1993).

S.-K. Yao, et al., American Physiol. Soc., *Thrombin Inhibition Enhances Tissue Type Plasminogen* . . . , pp. 374–379, (1992).

S.-Y. Yue, et al., Protein Engineering, *Characterization of the Interactions of a Bifunctional Inhibitor* . . . , vol. 5, No. 1, pp. 77–83, (1992).

T. Rydel, et al., Reports, *The Structure of a Complex of Recombinant Hirudin and Human α–Thrombin*, pp. 277–280, (Jul. 1990).

J. Schneider, Thrombosis Research, *Heparin and the Thrombin Inhibitor* . . . , vol. 64, No. 9, pp. 677–687, (1991).

G. Steffens, et al., Hoppe–Seyler's Z. Physiol. Chem., *The Complete Amino Acid Sequence of Low Molecular Mass Urokinase from Human Urine*, Bd. 363, S. 1043–1058, (Sep. 1982).

D. Stump, et al., J. of Biol. Chem., *Urokinase–Related Proteins in Human Urine*, vol. 261, No. 3, pp. 1267–1269, (1986).

A. Szczeklik, et al., Arteriosclerosis and Thrombosis, *Persistent Generation of Thrombin After Acute Myocardial Infarction*, vol. 12, No. 5, pp. 548–553, (May 1992).

U. Tebbe, et al., Z. Kardiol. 80, Suppl. 3, 32–32 (1991).

M. Mellott, et al., Arteriosclerosis and Thrombosis, *Vampire Bat Salivary Plasminogen* . . . , vol. 12, No. 2, pp. 212–221, (Feb. 1992).

German Abstract, DE 41 37 996, (May 27, 1993).

S. Gardell, et al., J. of Biol. Chem., *Isolation, Characterization and cDNA Cloning of a Vampire Bat* . . . , vol. 264, No. 30, pp. 17947–17952, (1989).

A. Gruber, et al., Circulation, *Antithrombotic Effects of Combining Activated Protein C and Urokinase in Nonhuman Primates*, vol. 84, No. 6, pp. 2454–2462, (Dec. 1991).

P. Eisenberg, Circulation, *Balance of Procoagulant and Fibrinolytic Activity*, vol. 84, No. 6, pp. 2601–2603, (Dec. 1991).

R. Flohe, Appl. Microbiol. Biotechnol, *High Expression Vectors for the Production of Recombinant Single–Chain Urinary Plasminogen Activator from Escherichia coli*, vol. 36, pp. 640–649, (1992).

D. Collen, et al., Thrombosis and Haemostasis, *Thrombolytic and Pharmacokinetic Properties of Human Tissue-–Type Plasminogen Activator Variants* . . . , vol. 6, No. 2, pp. 174–180, (1991).

D. Collen, et al., Blood, *Basic and Clinical Aspects of Fibrinolysis and Thrombolysis*, vol. 78, No. 12, pp. 3114–3124, (Dec. 15, 1991).

H.R. Lijnen, et al., Thrombosis and Haemostasis, *Strategies for the Improvement of Thrombolytic Agents*, vol. 66, No. 1, pp. 88–110 (1991).

J. Krstenansky, et al., J. Med. Chem., *Anticoagulant Peptides*: . . . , vol. 30, pp. 1688–1691, (1987).

H. Heyneker et al., Genetics of Industrial Microorganisms, *Expression of Human Urokinase Gene in E. coli*, pp. 214–221, (1982).

H. Lijnen, et al., J. of Biol. Chem., *Activation of plasminogen by Pro–Urokinase*, vol. 261, No. 3, pp. 1253–1258, (1986).

J. Maraganore, et al., Biochemistry, *Design and Characterization of Hirulogs*: . . . , vol. 29, pp. 7095–7101, (1990).

W. Günzler, et al., Hoppe–Seyler's Z. Physiol. Chem., *The Primary Structure of High Molecular Mass Urokinase from Human Urine*, Bd. 363, S. 1155–1165, (Oct. 1992).

H. Lu, et al., Blood, *Comparative Thrombolytic Properties of Bolus Injections and Continuous Infusions of a Chimeric* . . . , vol. 78, No. 1, pp. 125–131, (Jul. 1, 1991).

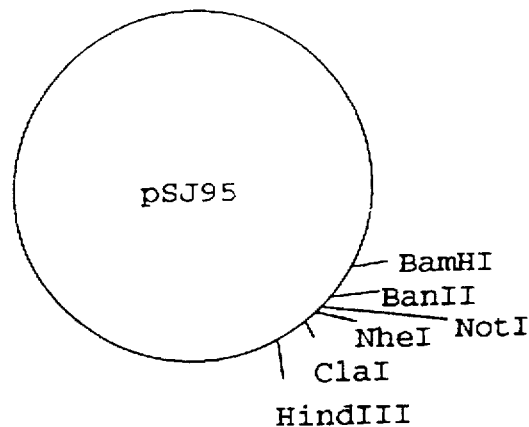
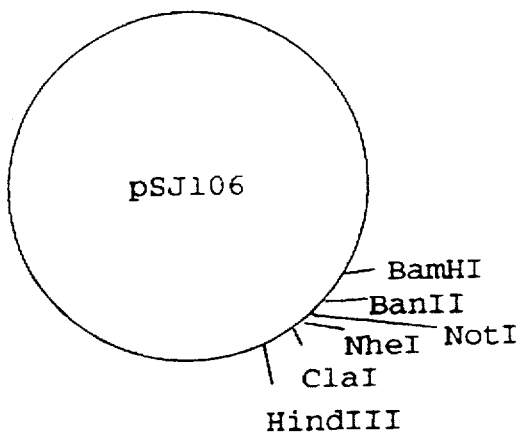
Figure 2o

BIFUNCTIONAL UROKINASE VARIANTS WITH IMPROVED FIBRINOLYTIC CHARACTERISTICS AND THROMBIN INHIBITING EFFECT

This application is a division of co-pending application Ser. No. 08/093,741, filed Jul. 20, 1993.

The invention relates to bifunctional variants of urokinase with improved fibrinolytic properties and thrombin-inhibiting activity, to the plasmids used in the production of these polypeptides, as well as to thrombolytic agents which contain bifunctional variants of urokinase as an active ingredient.

An important property of human blood is its ability to block lesions to the circulatory system by forming clots. Blood clotting is caused by a number of enzymes which are present in blood, and which, in the so-called clotting cascade, lead finally to the proteolytic conversion of the precursor protein, fibrinogen, to fibrin by the enzyme thrombin. Fibrin polymerizes together with thrombocytes, erythrocytes and other blood components at the site of the lesion, forming a clot.

In addition, blood also contains a series of enzymes which counteract the clotting process, and ensure the blood flow after regeneration of the vessel walls. The most important enzyme for the thrombolysis is plasmin, which attacks the fibrin network and so causes the dissolution of the clot. Plasmin is produced by proteolytic cleavage of the inactive precursor protein, plasminogen. This activation is performed by plasminogen activators which cleave plasminogen proteolytically. Two endogenous human plasminogen activators are known: urokinase, a plasminogen activator which is found in urine, and tissue plasminogen activator.

Cardiac infarcts and cerebral strokes are closely linked to the pathological formation of clots. In both types of infarct, clots are formed on the vessel walls under certain conditions—mostly as a result of arteriosclerotic alterations of the arteries. These clots can disturb the blood flow in the arteries, so that tissues can no longer be supplied with sufficient oxygen. After a cardiac infarct, this leads to a partial or complete necrosis of the heart muscle. Correspondingly, blockage of cerebral arteries leads to severe damage of the brain tissue.

Plasminogen activators are employed as thrombolytic agents in the therapy of infarct patients, in order to start the dissolution of the clots by plasmin. At present, streptokinase, APSAC (anisoylated plasminogen-streptokinase activator complex), two-chain urokinase (UK), recombinant single-chain urokinase (recombinant prourokinase) and tissue plasminogen activator (tPA) are available for such therapies (Collen and Lijnen, Blood 78, 3114–3124 (1991)). Streptokinase is a protein isolated from hemolytic streptococci. Streptokinase activates plasminogen by forming a complex with the plasminogen, which converts the plasminogen to an active structure. This complex can then convert free plasminogen to plasmin, which in turn cleaves the streptokinase-complexed plasminogen. A further development related to streptokinase is APSAC, a synthetic complex containing streptokinase and human plasminogen. Because the active site of the plasminogen is chemically modified, APSAC has a longer biological half-life than streptokinase.

Urokinase is a human protein which can be recovered from urine in two forms which are proteolytically active: these are high molecular weight urokinase (HUK), and low molecular weight urokinase (LUK) (Stump et al., J. Biol. Chem. 261, 1267–1273 (1986). HUK and LUK are two-chain molecules. Urokinase is synthesized by various tissues as single-chain urokinase (prourokinase) which can be detected at low levels in human blood (Wun et al., J. Biol. Chem. 257, 3276–3282 (1982)). The activated form of prourokinase has, as HUK, a molecular mass of 54 Kilodaltons, and contains three domains: an amino-terminal growth factor domain, a Kringle, and a serine protease domain (Guenzler et al., Hoppe-Seyler's Z. Physiol. Chem. 363, 1155–1165 (1982); Steffens et al., Hoppe-Seyler's Z. Physiol. Chem. 363, 1043–1058 (1982)). Although both prourokinase and plasminogen are present as proenzymes, prourokinase possesses an intrinsic activity which enables it to convert plasminogen into active plasmin. However, this plasminogen activator becomes first fully active after the plasmin which has been formed, for its part has cleaved the prourokinase between $^{158}$lysine and $^{159}$isoleucine (Lijnen et al., J. Biol. Chem. 261, 1253–1258 (1986)). The production of urokinase by gene technology in Escherichia coli was first described by von Heyneker (Proceedings of the IVth International Symposium on Genetics of Industrial Microorganisms 1982). Non-glycosylated prourokinase (saruplase) is presently produced using a synthetic gene (Brigelius-Flohe et al., Appl. Microbiol. Biotech. 36, 640–649 (1992)).

Tissue plasminogen activator is a protein found in blood and in tissue which has a molecular mass of 72 Kilodaltons. This plasminogen activator possesses 5 domains: an amino-terminal "finger" domain, a growth factor domain, Kringle 1, Kringle 2, and the serine protease domain. In contrast to prourokinase, tPA is able to cleave plasminogen only after binding to fibrin. Similar to prourokinase, tPA can be converted to an active form by a plasmin-catalyzed cleavage between Kringle 2 and the serine protease domain. During this process, tissue plasminogen activator binds to fibrin, but not to fibrinogen, so that plasminogen is activated in a clot-specific manner and, in contrast to two-chain urokinase, a general plasminogen activation is largely prevented (Collen and Lijnen, Blood 78, 3114–3124 (1991)).

Since the beginning of the 80's, active treatment of myocardial infarct with thrombolytic agents has been proven to be effective and efficient. In a number of studies it was shown that treatment of patient suffering from myocardial infarct with streptokinase, APSAC, UK, recombinant prourokinase or tPA leads to a significant reduction of mortality in comparison to non-treated patients. In order to improve the effectiveness of this type of therapy, a number of derivatives of tissue plasminogen activator and of prourokinase have been synthesized using gene technology. Next to the aims of increasing the fibrinolytic activity and of reducing side-effects, of central interest is the search for forms suitable for bolus applications. Reviews of the lines of thought which could lead to improvements of plasminogen activators are to be found in Thrombosis and Haemostasis 66, 88–110 (1991) and in Trends in Biotech. 9, 86–90 (1991).

In attempts to improve the effectiveness of plasminogen activators, and in particular to increase their biological half-lives, deletion and substitution variants of tissue plasminogen activator were synthesized in which, for example, the "finger" and the growth factor domains were removed, or the serine protease domain exchanged for that of urokinase (Collen et al., Thromb. Haemostasis 65, 174–180 (1991); Fromage et al., Fibrinolysis 5, 187–190 (1991); Lu et al., Blood 78, 125–131 (1991)). It could be shown that deletion of the "finger" and growth factor domains lead to an increase in the biological half-life of the tPA variants (Lijnen and Collen, Thromb. Haemostasis 66, 94–95 (1991)). Another variant, consisting of both Kringle domains of tPA attached to the serine protease domain of urokinase, was superior to unmodified plasminogen activators because of its significantly longer half-life. These variants, however, showed only a weak fibrin specificity (Lu et al., Blood 78, 125–131 (1991))

Various attempts have been made to synthesize plasminogen activator variants with increased fibrin specificity. In order to reduce the risk of bleeding, such variants should activate plasminogen only in the vicinity of a clot, and not lead to a systemic activation of plasminogen. For example, one variant of tPA is known in which Kringle 1 has been exchanged by Kringle 2 of the original molecule. This variant has an increased affinity for N-terminal lysine residues but not for fibrin. In animal experiments, this variant was no more effective than the original tissue plasminogen activator (Collen et al., Thromb. Haemostasis 65, 174–180 (1991)). Other known variants, which result from the fusion of a clot-specific antibody and a plasminogen activator, are more effective in animal models than the original plasminogen activator (Lijnen and Collen, Thromb. Haemostasis 66, 88–110 (1991)). A plasminogen activator isolated from a bat, Desmodus retundus, has an extremely high fibrin specificity (Gardell et al., J. Biol. Chem. 264, 17947–17952 (1989)). This plasminogen activator had an improved thrombolytic activity, and an increased half-life, and showed reduced systemic plasminogen activation when compared to tPA in animal experiments (Gardell et al., Circulation 84, 244–253 (1991); Mellott et al., Arterioscl. Thromb. 12, 212–221 (1992)).

The success of the treatment of infarct patients with plasminogen activators depends however not only on the clot lysis, but also upon the extent to which re-occlusion of opened blood vessels can be prevented. Various findings suggest that thrombin, which is bound within the clot, is set free as an active enzyme on clot lysis, and can induce the re-occlusion of blood vessels (Szczeklik et al., Arterioscl. Thromb. 12, 548–553 (1992); Eisenberg, Circulation 84, 2601–2603 (1991)). It is known that the efficiency of thrombolytic agents is improved by simultaneous medication, or premedication, with the thrombin inhibitor heparin. Likewise, application of Argatroban, Hirugen or Protein C can also reduce the tendency towards re-occlusions after lysis therapy (Schneider, Thromb. Res. 64, 677–689 (1990); Yao et al., Am. Physiol. 262 (Heart Circ. Physiol. 31, H 374–H 379 (1992), Gruber et al., Circulation 84, 2454–2462 (1991)). Furthermore it is known that the mortality rate among infarct patients who were treated with heparin prior to application of prourokinase is significantly diminished in comparison to the mortality among a control group who received prourokinase without heparin pretreatment (Tebbe et al., Z. Kardiol. 80, Suppl. 3, 32 (1991)).

One of the most potent inhibitors of thrombin is hirudin, which can be isolated from the leech Hirudo medicinales. Hirudin binds to the so-called anion-binding site of thrombin via its carboxyl-terminal part. Particular amino acids in the amino-terminal part of hirudin block the entrance to the substrate binding pocket of thrombin (Rydel et al., Science 249, 277–280 (1990)). It is known that thrombin can also be inhibited by smaller derivatives of hirudin, and in particular by the hirulog molecule type described by Maraganore et al. in Biochemistry 29, 7095–7101 (1990) (see also Krstenansky et al., J. Med. Chem. 30, 1688–1691 (1987); Yue et al., Protein Engineering 5, 77–85 (1992)).

The use of hirudin in combination with a plasminogen activator for the treatment of blood vessel diseases arising from thromboses has been described in the European patent applications EP 328,957 and EP 365,468. The therapeutic use of hirudin derivatives in combination with a thrombolytic agent is known from the international patent application WO 91/01142.

Thrombin can also be inhibited by a peptide related to the amino-terminal sequence of the human thrombin receptor (Vu et al., Nature 253, 674–677 (1991) ). The thrombin receptor contains a thrombin-binding sequence in its amino-terminal region which is next to a cleavage point for thrombin.

The thrombin-binding region of the receptor has a structure which is very similar to that of the carboxyl-terminal region of hirudin. The receptor is activated by thrombin on cleavage of the receptor sequence. By mimicking the interaction between the receptor and thrombin, a fragment of the receptor containing the binding region and a modified cleavage point functions as a thrombin inhibitor.

Similarly, thrombin can be inhibited by a peptide derived from the amino acids 41 to 57 of haemadin (Strube et al, J. Biol. Chem. 268, 8590–8595 (1993)).

Object of the invention was the development of substances suitable for the treatment of blood vessel occlusions which result from clotting. These substances should be capable of inducing a complete clot lysis within a very short time, and at the same time be capable of hindering the re-occlusion of the blood vessels subsequent to a successful thrombolysis. Further, the use of these substances should not lead to a systemic plasminogen activation.

It has now been found that these extremely stringent criteria for a new substance are met by certain bifunctional urokinase variants.

Accordingly the present invention relates to bifunctional urokinase variants of formula I

wherein

M4 represents the amino acid sequence from $^{47}$Ser to $^{411}$Leu of the unglycosylated prourokinase according to FIG. 1, X$_1$ represents either a peptide bond, or
a peptide of the sequence
Ser-Pro-Pro-Ser-Pro-Pro-Gly-Gly-Phe (SEQ ID NO:1) or
Ser-Pro-Pro-Ser-Pro-Pro-Ser-Pro-Pro-Gly-Gly-Phe (SEQ ID NO:2) or
Ser-Pro-Pro-Ser-Pro-Pro-Ser-Pro-Pro-Gly-Gly-Phe-Gly (SEQ ID NO:3) or
a peptide sequence of formula II

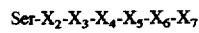

wherein X$_2$ is Pro or Leu, X$_3$ is Val or Pro, X$_4$ is Lys, Val, Arg, Gly or Glu, X$_5$ is Ala, Val, Gly, Leu or Ile, X$_6$ is Phe, Trp, Tyr or Val, and X$_7$ is a peptide bond or Gly, and Y$_1$ represents either a peptide of the sequence
Y$_2$-Arg-Pro-Y$_3$-Gly-Gly-Gly-Gly-Asn-Gly-Asp-Phe-Glu-Glu-Ile-Pro-Glu-Glu-Tyr-Leu-Y$_4$ (SEQ ID NO:4) or
Y$_2$-Arg-Pro-Phe-Leu-Leu-Arg-Asn-Pro-Asn-Asp-Lys-Tyr-Glu-Pro-Phe-Trp-Glu-Asp-Glu-Glu-Lys-Asn-Glu (SEQ ID NO:5) or
Y$_2$-Arg-Pro-Ser-Ser-Glu-Phe-Glu-Glu-Phe-Glu-Ile-Asp-Glu-Glu-Glu-Lys (SEQ ID NO:6)
wherein Y$_2$ is Pro or Val, Y$_3$ is Leu or a peptide bond and Y$_4$ is Gln or a hydroxyl group.

In the bifunctional urokinase variants of formula I in which

Y$_1$ represents a peptide of the sequence

Y$_2$-Arg-Pro-Y$_3$-Gly-Gly-Gly-Gly-Asn-Gly-Asp-Phe-Glu-Glu-Ile-Pro-Glu-Glu-Tyr-Leu-Y$_4$ (SEQ ID NO:4)

wherein Y$_2$ is Pro or Val, Y$_3$ is Leu or a peptide bond, and Y$_4$ is Gln or a hydroxyl group. X$_1$ preferably represents a peptide sequence of formula II Ser-X$_2$-X$_3$-X$_4$-X$_5$-X$_6$-X$_7$ in which X$_2$ is Pro or Leu, X$_3$ is Val, X$_4$ is Lys, Val or Arg, X$_5$ is Ala, Val or Gly, X$_6$ is Phe, Trp, Tyr or Val, and X$_7$ is a peptide bond or Gly. Especially preferred are those bifunctional urokinase variants with a peptide sequence of formula II in which X$_2$ is Pro or Leu, X$_3$ is Val, X$_4$ is Lys or Val, X$_5$ is Ala or Val, X$_6$ is Phe, Trp or Tyr and X$_7$ is a peptide bond or Gly and in particular those bifunctional urokinase variants in which X$_7$ is a peptide bond.

In bifunctional urokinase variants of formula I, in which Y$_1$ represents a peptide with the sequence Y$_2$-Arg-Pro-Phe-Leu-Leu-Arg-Asn-Pro-Asn-Asp-Lys-Tyr-Glu-Pro-Phe-Trp-Glu-Asp-Glu-Glu-Lys-Asn-Glu (SEQ ID NO:5)

in which Y$_2$ is Pro or Val, X$_1$ preferably represents a peptide sequence of formula II Ser-X$_2$-X$_3$-X$_4$-X$_5$-X$_6$-X$_7$ in which X$_2$ is Pro or Leu, X$_3$ is Val, X$_4$ is Lys or Val, X, is Ala or Val, X$_6$ is Phe or Trp, and X$_7$ is a peptide bond.

In comparison to other known plasminogen activators, and to combinations of a plasminogen activator with a thrombin inhibitor, the bifunctional urokinase variants according to the invention distinguish themselves through a stronger fibrinolytic activity, combined with unprecedentedly good thrombin-inhibiting characteristics. Further to this, the decrease in plasma fibrinogen levels upon administration of the polypeptides of the invention was unexpectedly small. The significantly higher fibrin specificity, particularly in comparison to the known combinations of a plasminogen activator and a thrombin inhibitor, results in a minimal influence on the clotting ability of blood, and minimizes the danger of uncontrolled bleeding as a possible complication arising from systemic fibrinogen degradation.

The high fibrin specificity of the urokinase variants according to the invention therefore allows their application as a bolus with a much lower risk of bleeding in comparison to the bolus application of other known thrombolytic agents.

Bifunctional urokinase variants of formula I are toxicologically safe, so that they can be administered in appropriate pharmaceutical forms to patients suffering from occlusions of blood vessels resulting from clots.

Further subject matter of the invention are thrombolytic agents having a bifunctional urokinase variant of formula I as active ingredient.

For the treatment of occlusions of blood vessels caused by blood clots—e.g. cardiac infarct, cerebral infarct, acute occlusions of peripheral arteries, embolisms of the lung, and thromboses of deep leg or hip veins—0.1 to 1 mg/kg of one of the polypeptides according to the invention are required. The bifunctional urokinase variants may be intravenously administered especially by bolus injection.

The thrombolytic agents according to the invention contain at least one bifunctional urokinase variant together with adjuvants such as carrier materials, solvents, diluents, coloring agents and binding agents. The choice of and the amount of the adjuvants depends upon how the drug substance is to be administered, and presents no problem to an expert.

The bifunctional urokinase variants are produced by methods of gene-technology. Thus further subject matter of the invention are the plasmids used to obtain bifunctional urokinase variants of formula I, which contain an operon with a regulatable promotor, a Shine-Dalgarno sequence effective as a ribosomal binding site, a start codon, a synthetic structural gene coding for one of the bifunctional urokinase variants of formula I, and one or two terminators downstream of the structural gene.

The trp-promotor or the tac-promotor are particularly suitable as regulatable promotors. The trp A-terminator and/or the tet A/orf L terminator from Tn 10 are preferentially employed as terminators.

In the control region of the plasmids according to the invention, the distance between the Shine-Dalgarno sequence and the start codon is 6 to 12, preferably 8 to 10 nucleotides.

The expression of the plasmids according to the invention is performed in strains of Escherichia coli, preferably in strains of Escherichia coli of the group K12, for example *E.coli* K12 JM101 (ATCC 33876), *E.coli* K12 JM103 (ATCC 39403), *E.coli* K12 JM105 (DSM 4162) and *E.coli* K12 DH 1 (ATCC 33849). The bifunctional urokinase variants of formula I according to the invention are produced in high yields within the bacterial cells as inclusion bodies, in which the proteins are present in a denatured form. After isolation of the inclusion bodies, the denatured protein is refolded into the required tertiary structure by protein-chemical methods involving the use of a redox system.

EXAMPLES

Figure 2:
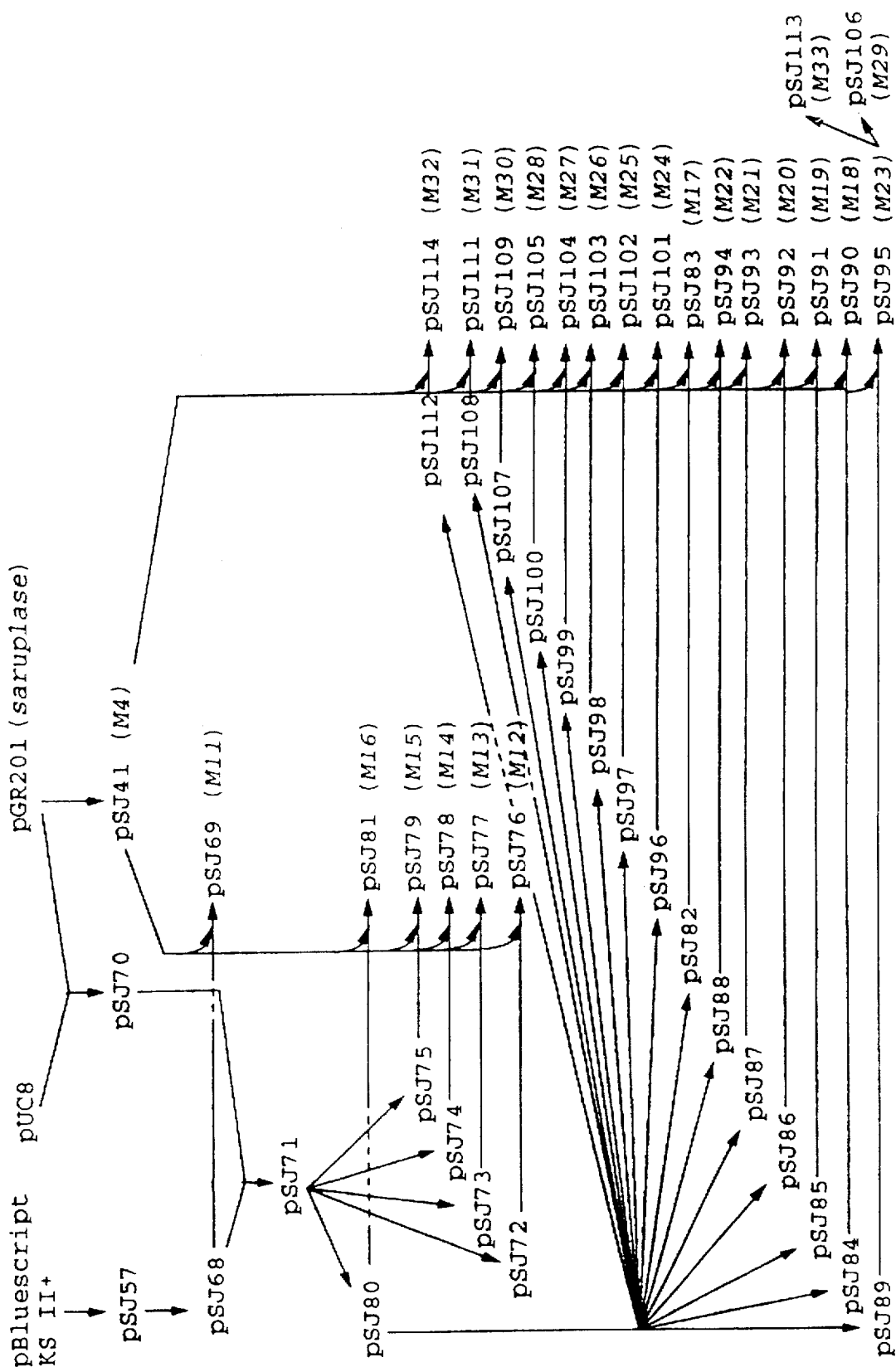
Figure 2A:
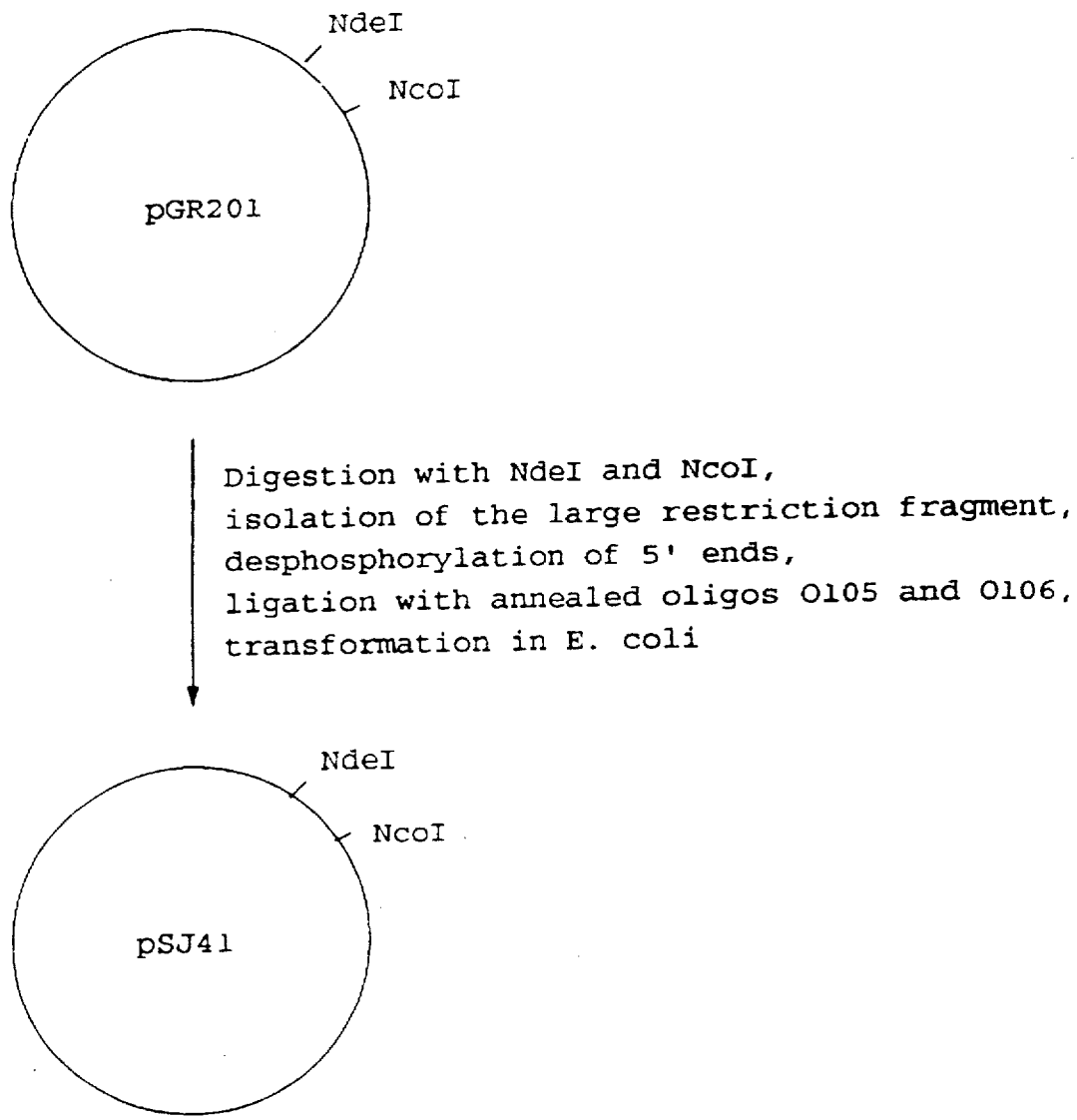
Figure 2B:
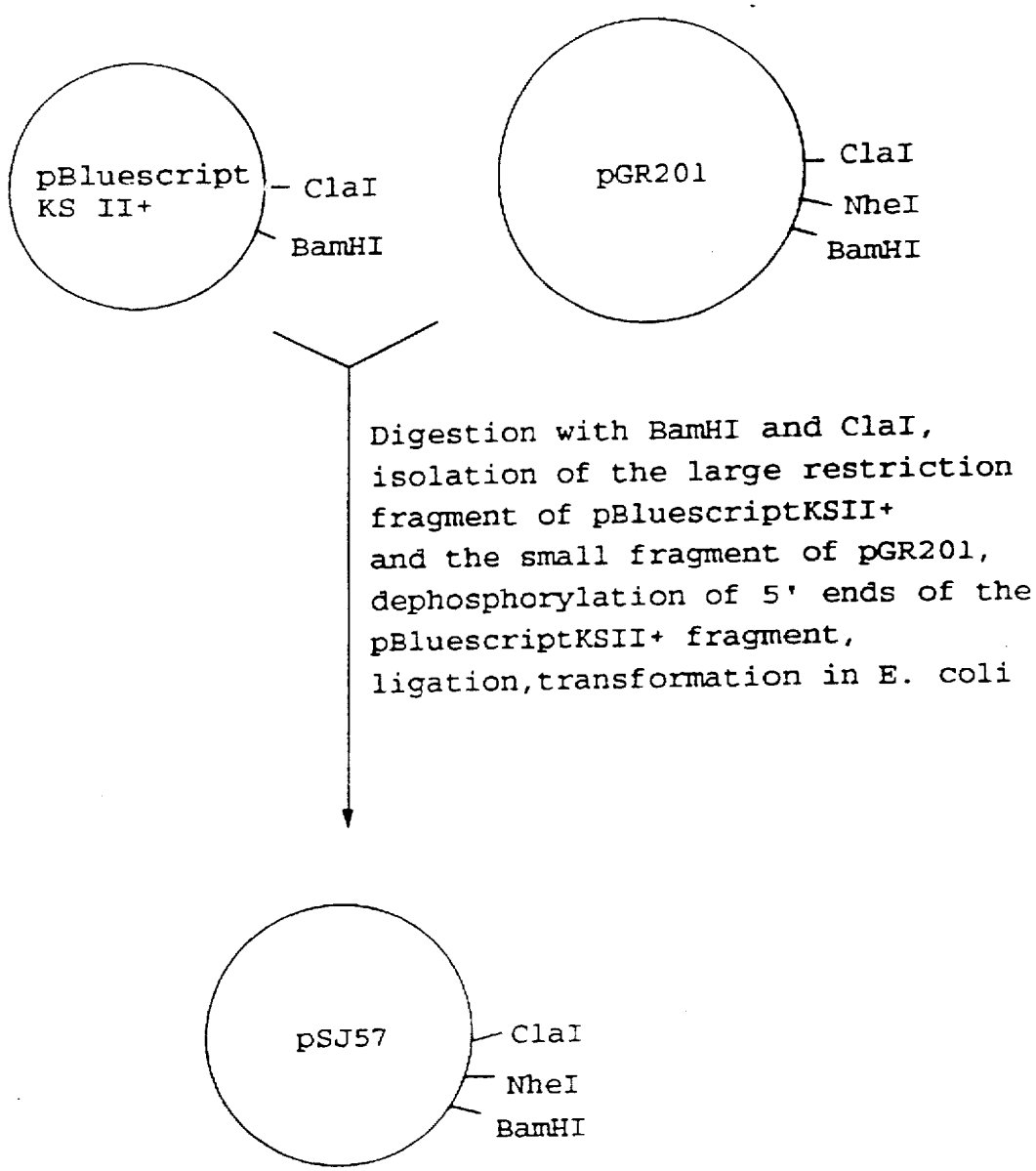
Figure 2C:
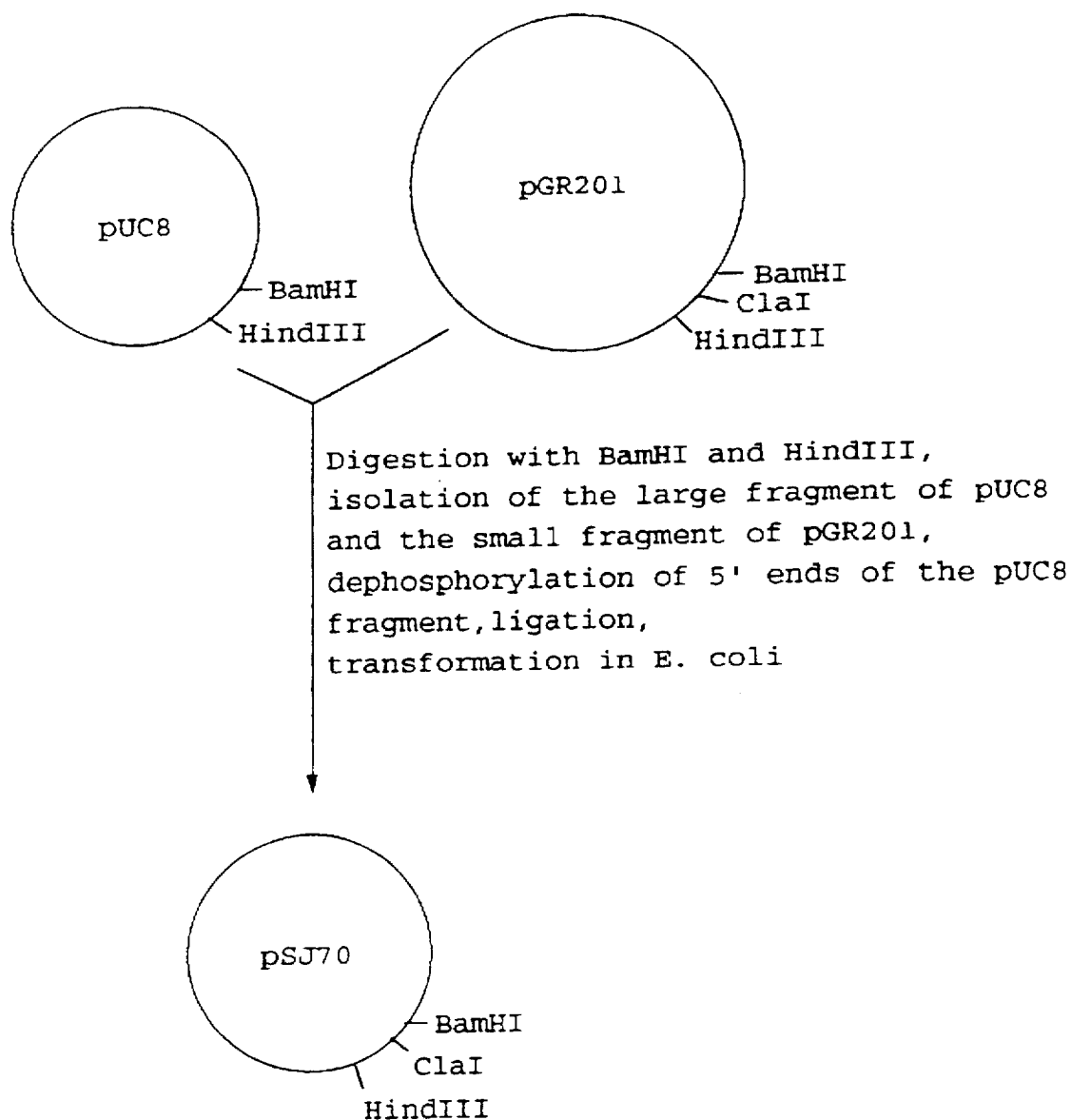
Figure 2D:
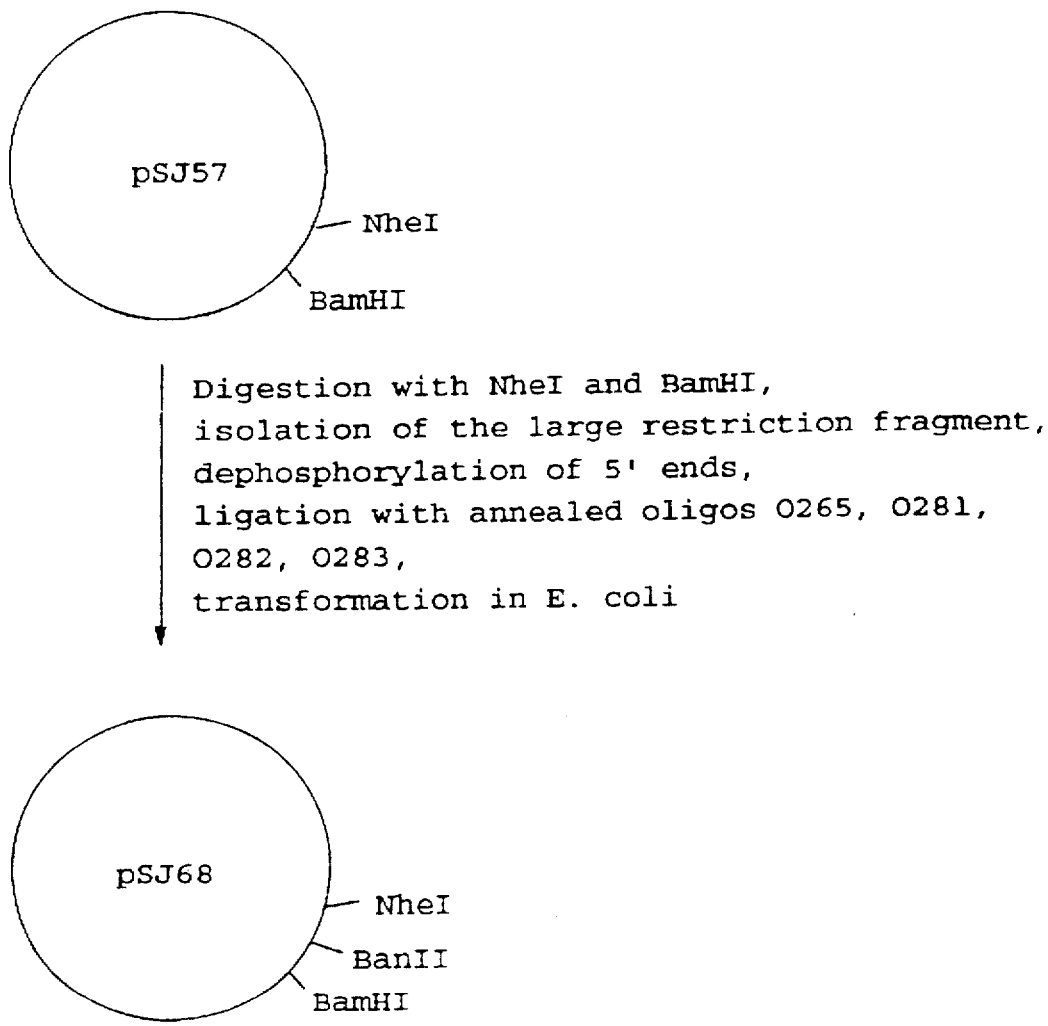
Figure 2E:
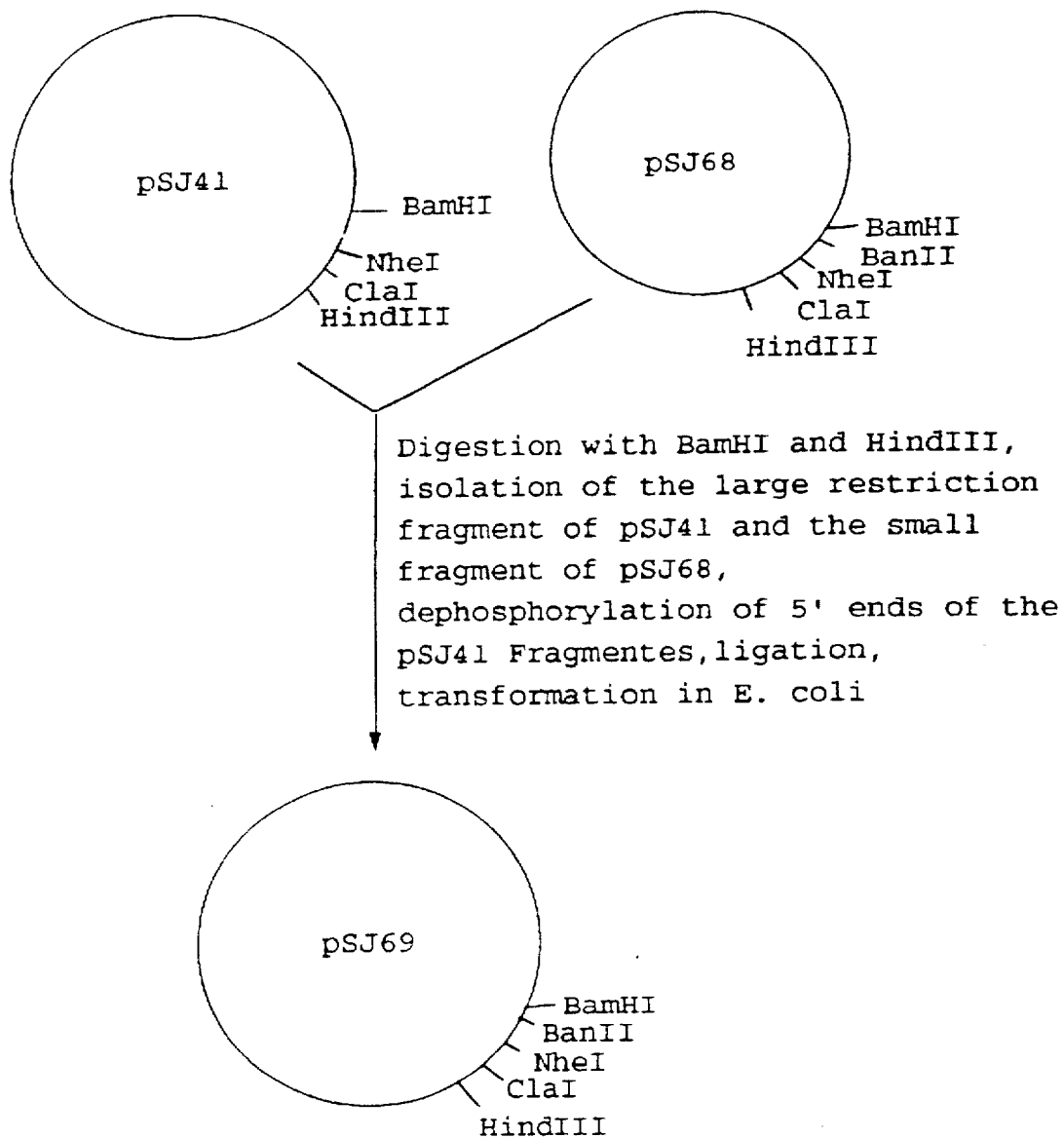
Figure 2F:
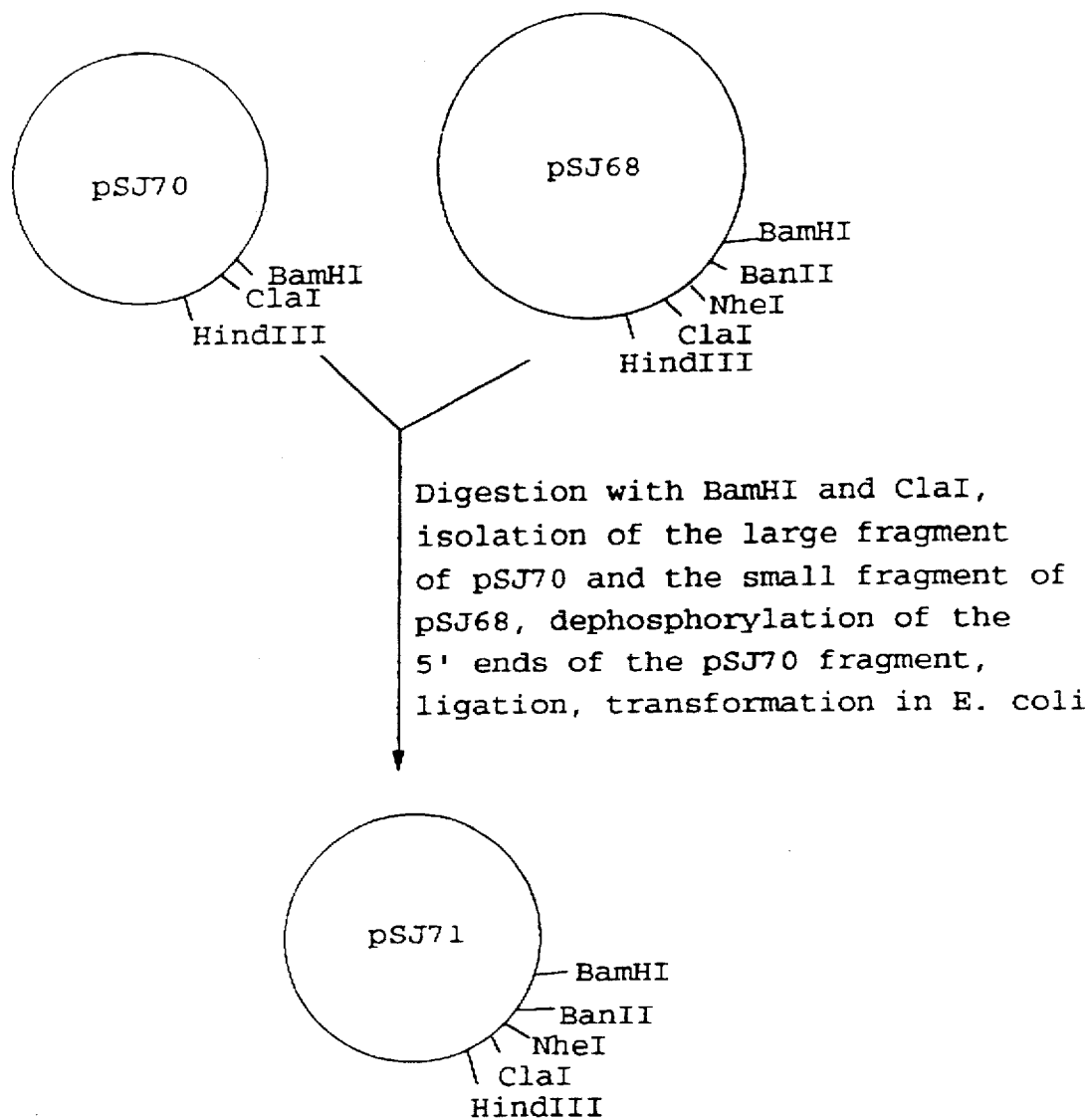
Figure 2G:
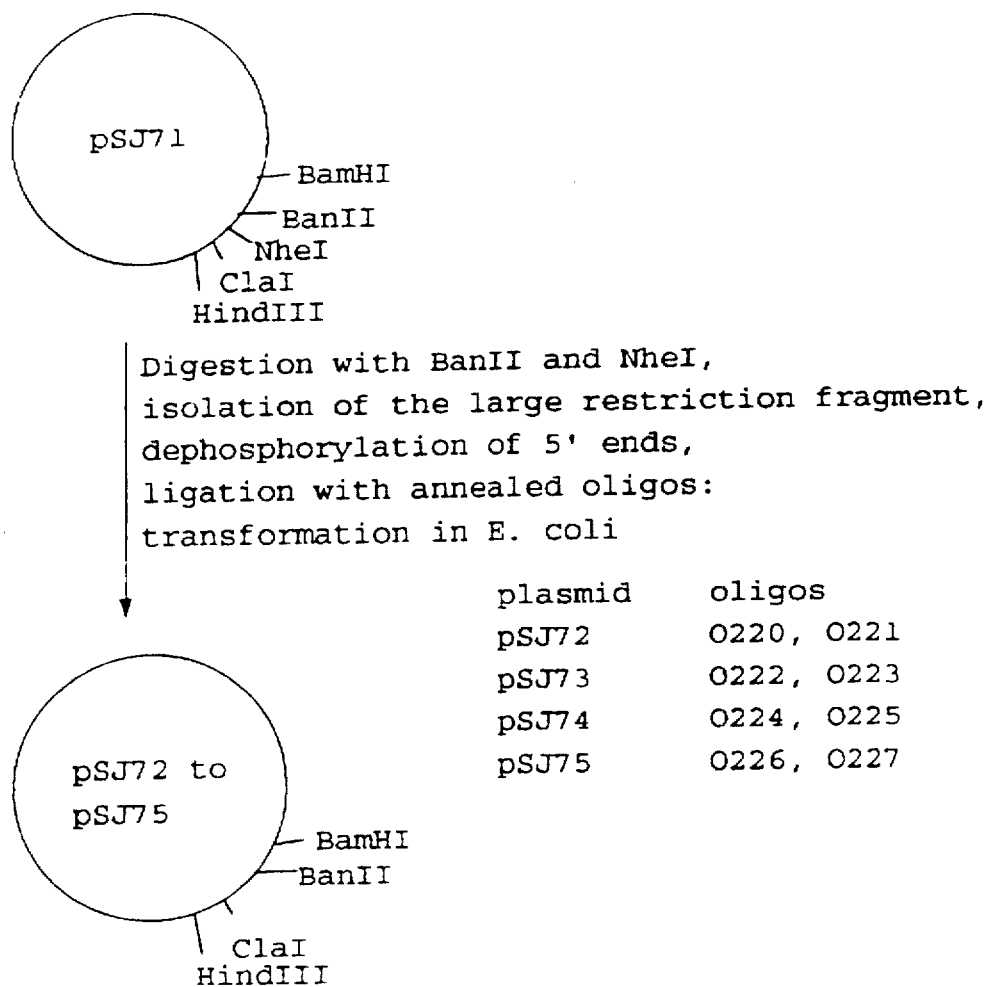
Figure 2H:
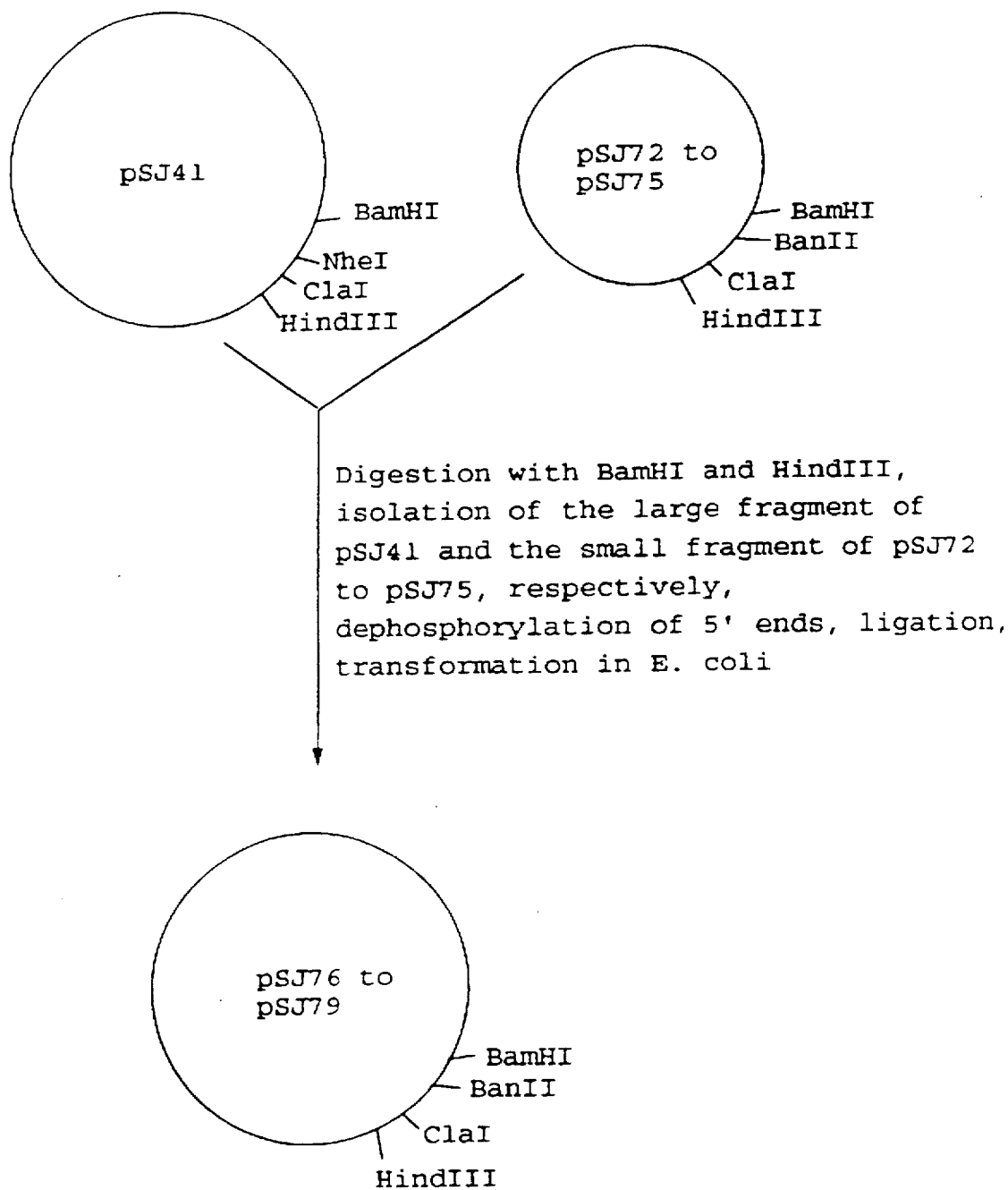
Figure 2I:
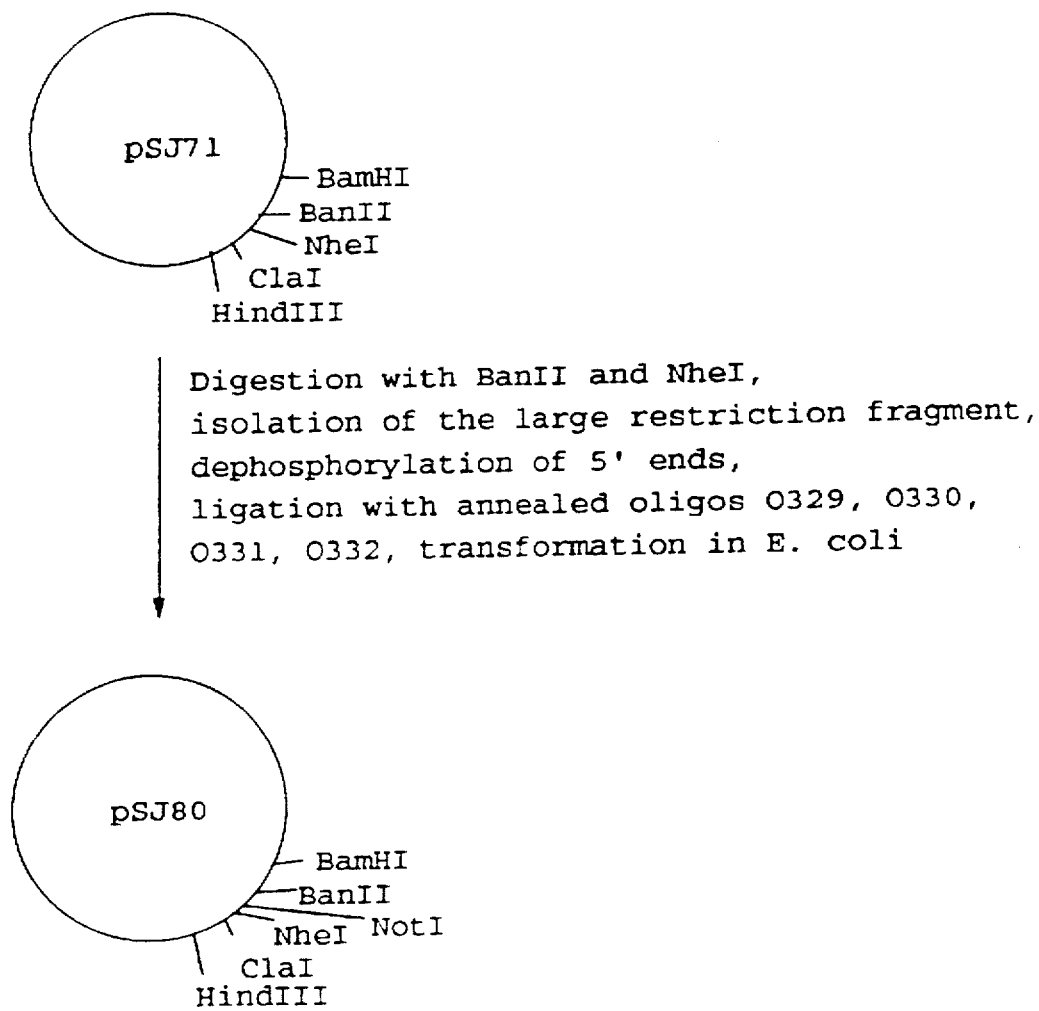
Figure 2J:
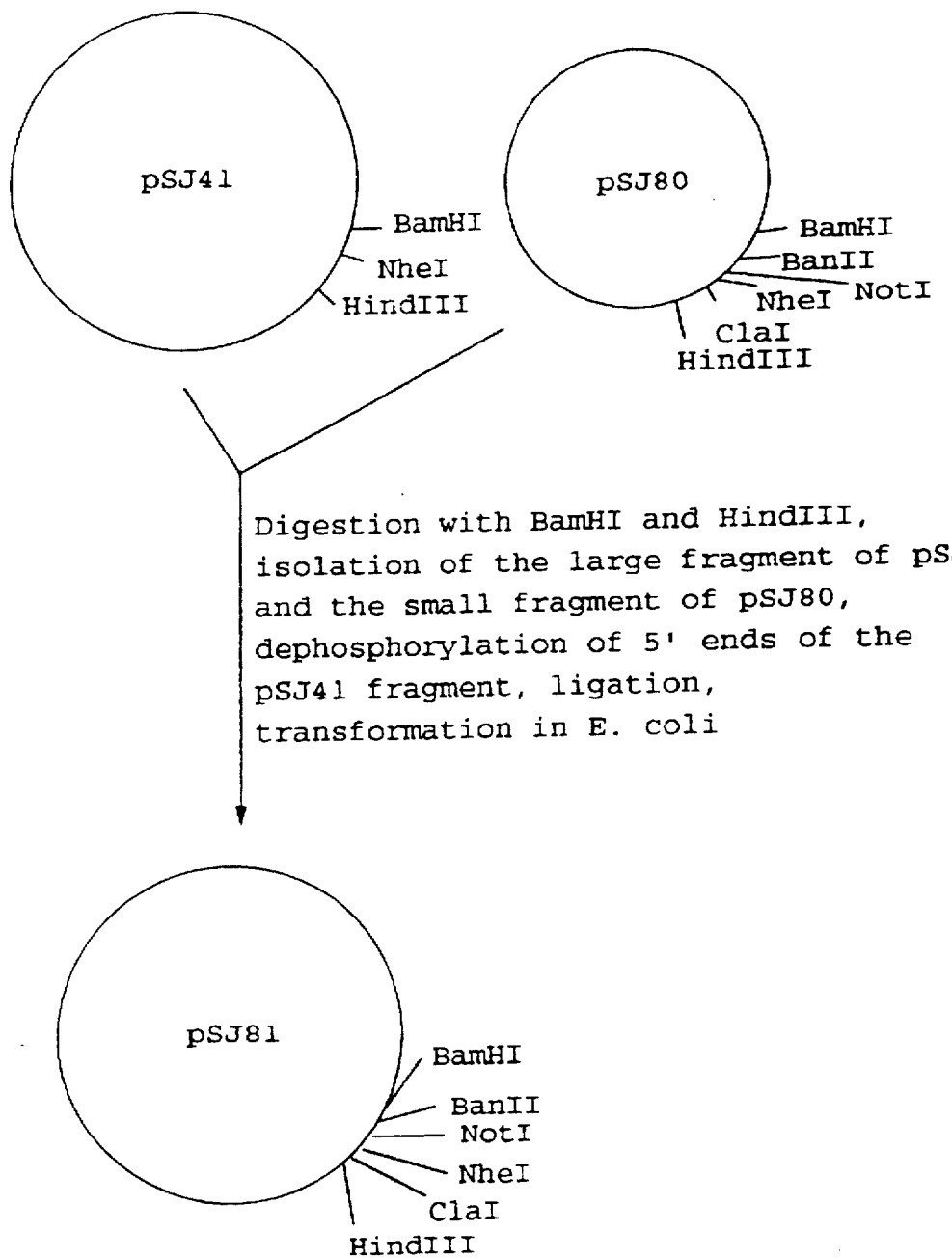
Figure 2K:
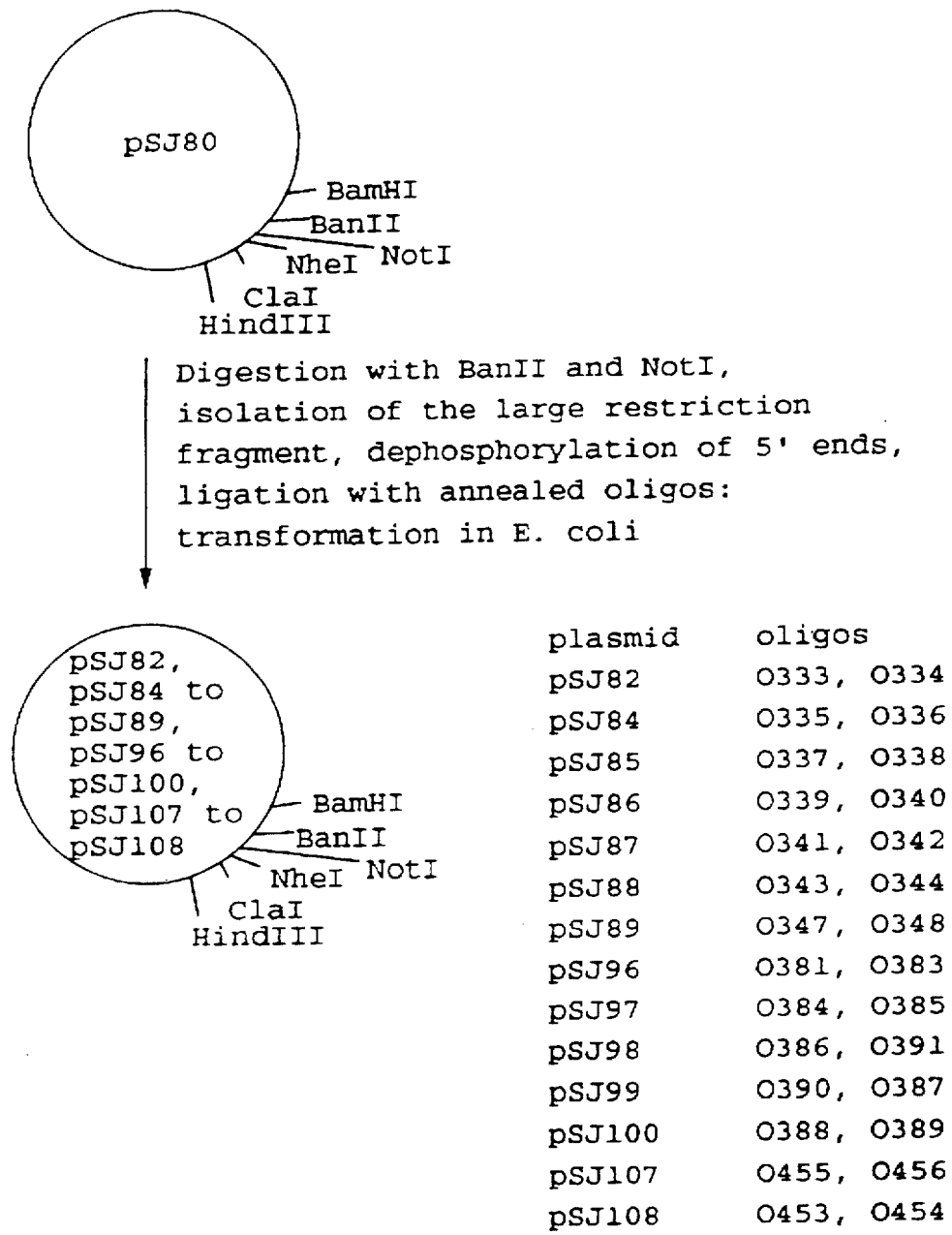
Figure 21:
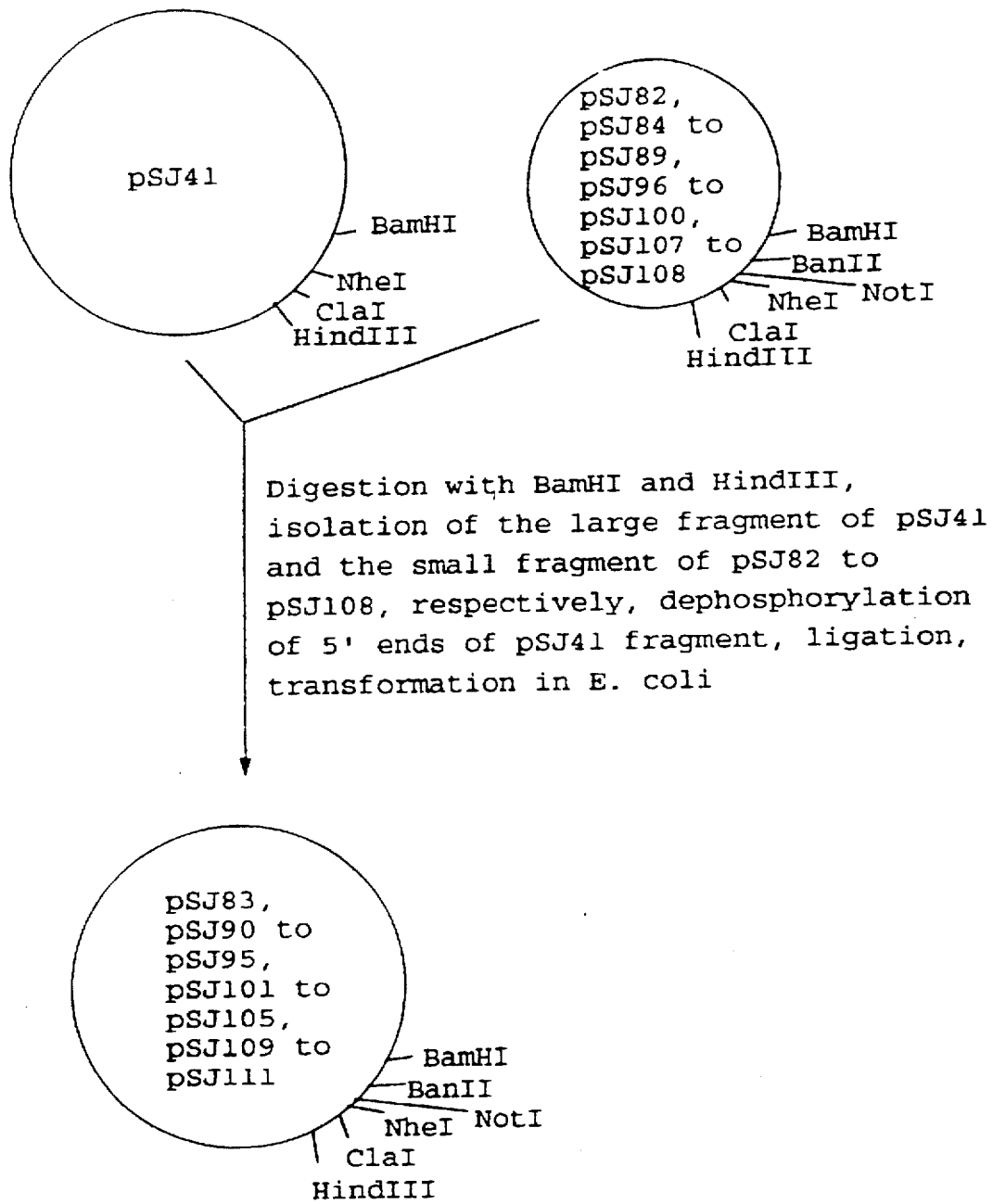
Figure 2M:
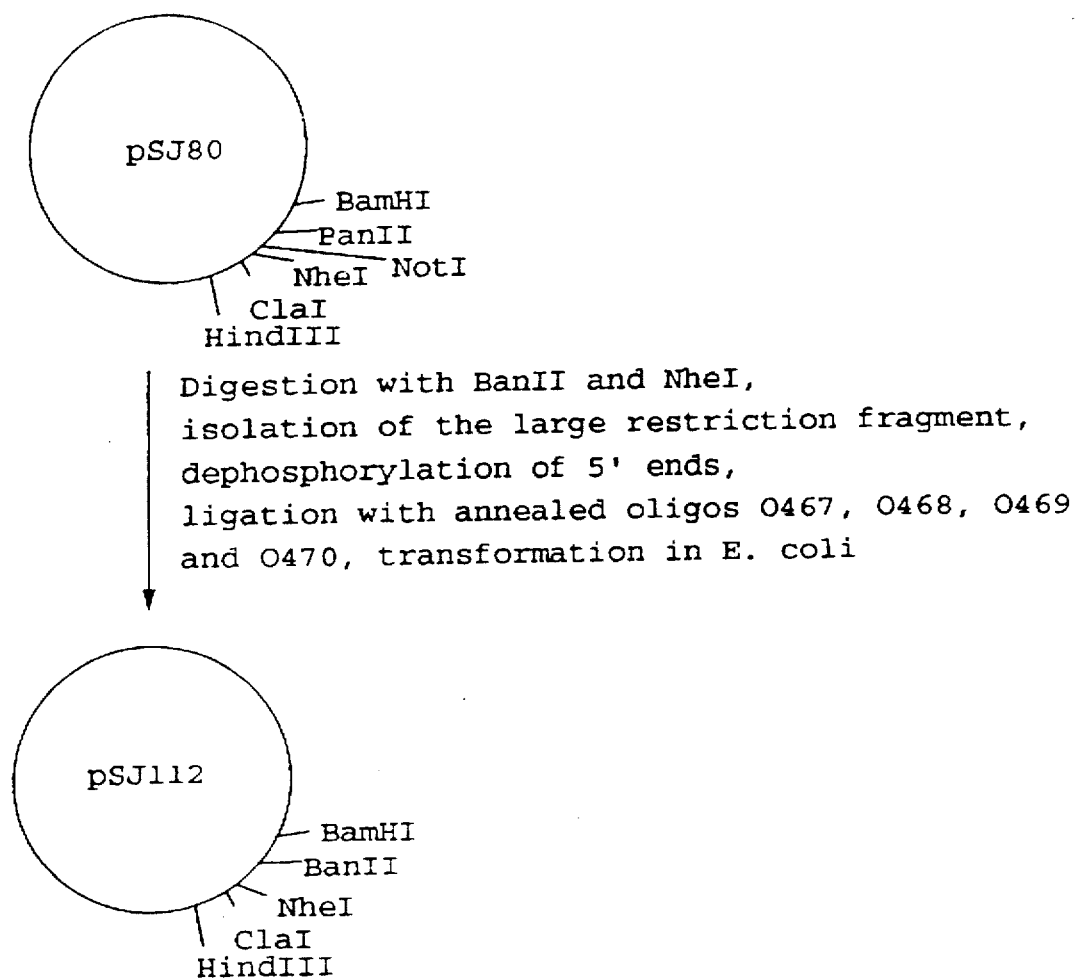
Figure 2N:
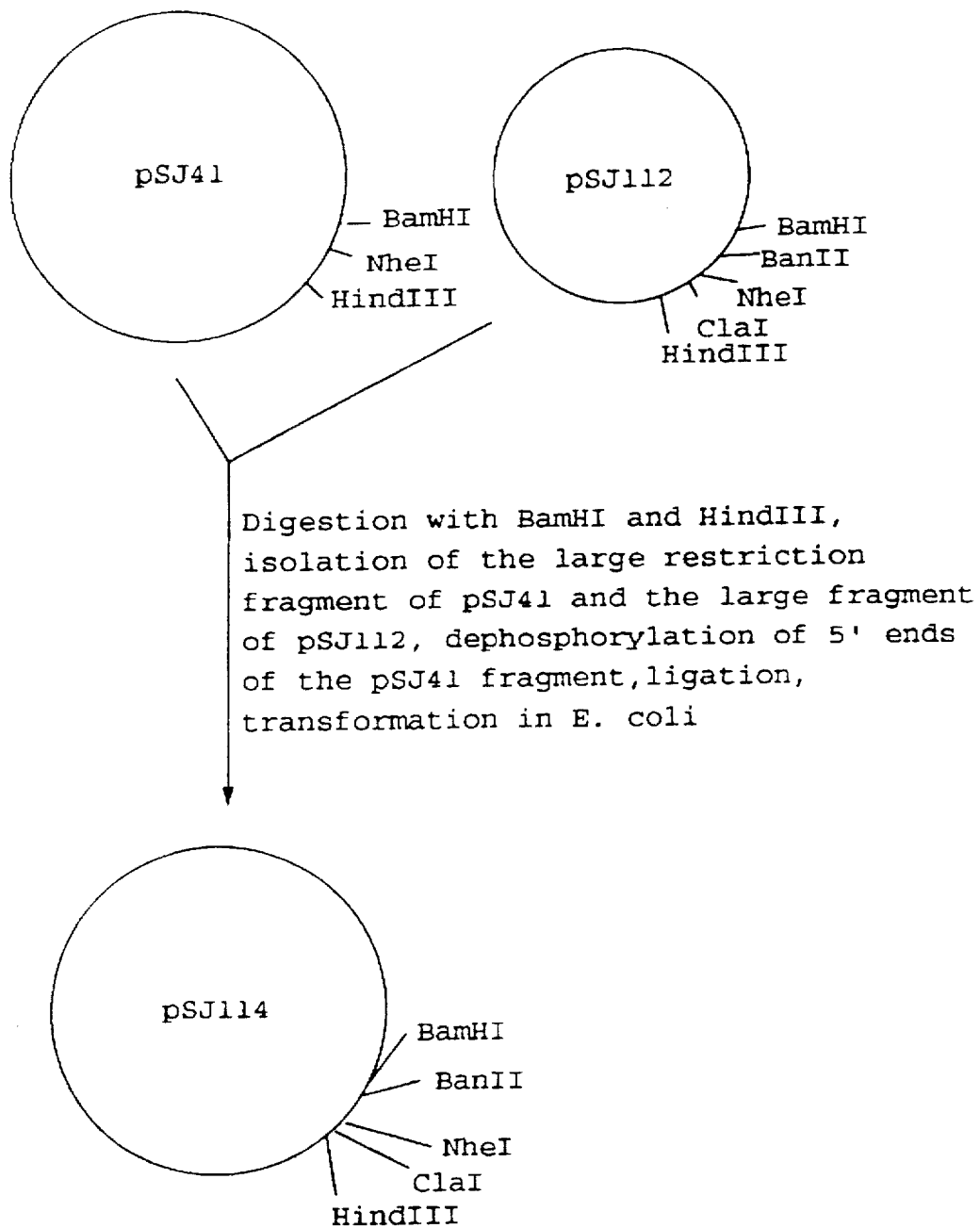
Figure 2P:
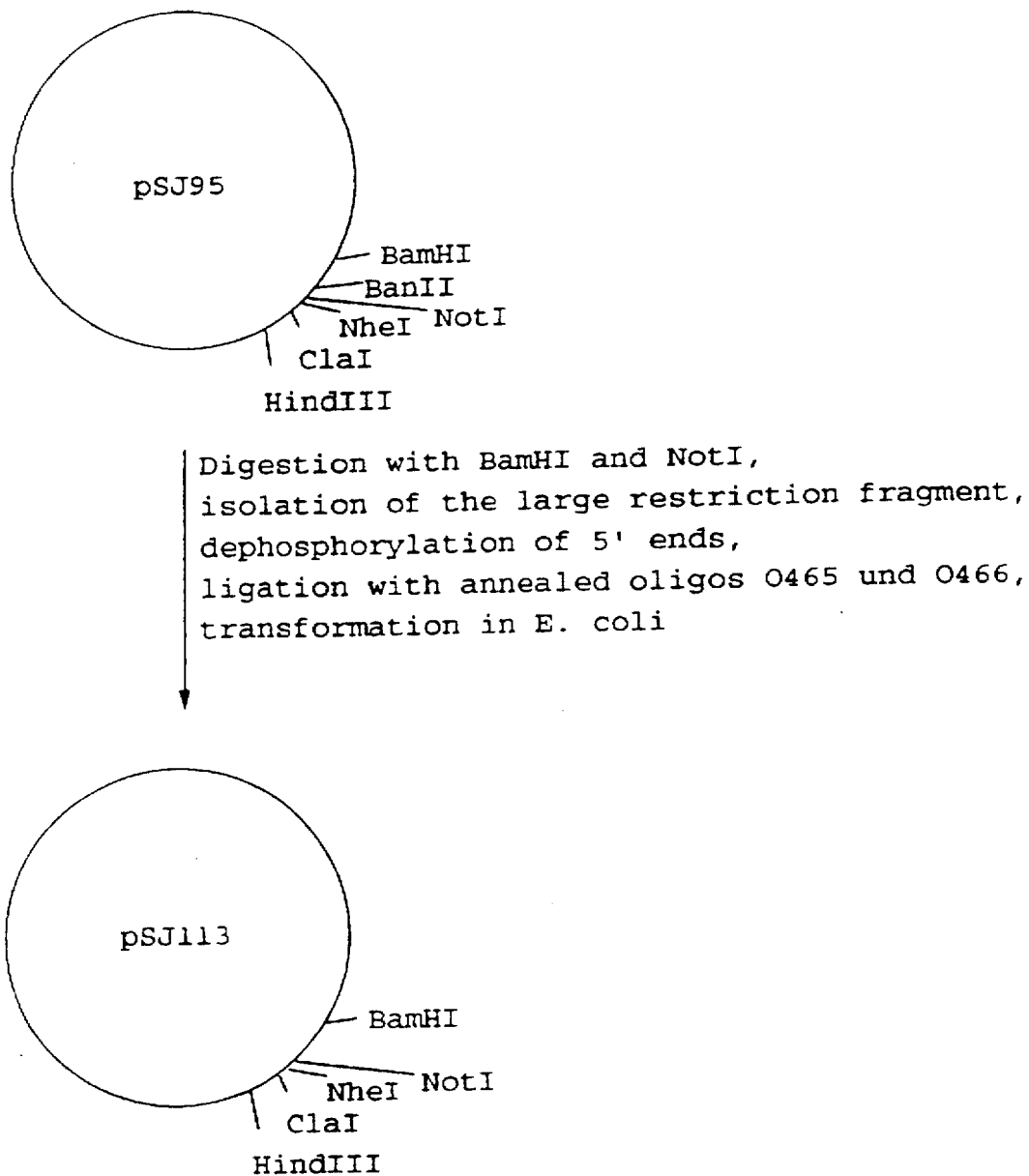

1) Production, isolation and purification of bifunctional urokinase variants according to the invention a) Cloning methods The expression plasmids for the gene technological production of the polypeptides according to the invention within Escherichia coli were constructed by known methods. The sequence of individual steps involved this construction is shown in FIG. 2, and FIGS. 2a to 2p. Starting materials for the plasmid construction were the plasmids pBlueskript KS II+(Stratagene, Heidelberg), pUC8 (Pharmacia, Freiburg), and pGR201. pGR201 is identical to the plasmid pBF160 which has been described in EP 408, 945 and in Appl. Microbiol. Biotechn. 36, 640 to 649 (1992). The restriction endonucleases BanII, BamHI, ClaI, HindIII, NcoI, NdeI, NheI, and NotI, as well as the DNA-modifying enzymes such as alkaline phosphatase, T4-ligase, T4-kinase and T7-polymerase were obtained from commercial sources such as Pharmacia, Stratagene, Boehringer Mannheim and Gibco (Eggenstein). The alterations to the plasmids during their construction were checked by restriction analysis and DNA-sequencing. The DNA-sequencing was performed according to the recommendations of the manufacturer (Pharmacia). Various oligonucleotides (oligos) were employed during the construction of the plasmids: their sequences, and code names are listed in the following Table 1.

TABLE 1

Oligo
Code Oligo Sequence (from 5' to 3')

0105 TATGAGCAAAACTTGCTACGAAGGTAACGGTCACTTCTA CCGTGGTAAGGCTTCTACCGACAC
(SEQ ID NO: 7)
0106 CATGGTGTCGGTAGAAGCCTTACCACGGTAGAAGTGACC

TABLE 1-continued

| Oligo Code | Oligo Sequence (from 5' to 3') |
|---|---|
| | GTTACCTTCGTAGCAAGTTTTGCTCA<br>(SEQ ID NO: 8) |
| 0220 | CGGTTAAGGCTTTCCCGAGGCCTGGTGGTGGTGGTAACG<br>GTGACTTCGAAGAAATCCCGGAAGAGTACCTGTGATAGG<br>ATCAA<br>(SEQ ID NO: 9) |
| 0221 | CTAGTTGATCCTATCACAGGTACTCTTCCGGGATTTCTT<br>CGAAGTCACCGTTACCACCACCACCAGGCCTCGGGAAAG<br>CCTTAACCGGGCT<br>(SEQ ID NO: 10) |
| 0222 | CGCCGAGCCCGCCGAGCCCGCCGGGTGGTTTCCCGAGGC<br>CTGGTGGTGGTGGTAACGGTGACTTCGAAGAAATCCCGG<br>AAGAGTACCTGTGATAGGATCAA<br>(SEQ ID NO: 11) |
| 0223 | CTAGTTGATCCTATCACAGGTACTCTTCCGGGATTTCTT<br>CGAAGTCACCGTTACCACCACCACCAGGCCTCGGGAAAC<br>CACCCGGCGGGCTCGGCGGGCTCGGCGGGCT<br>(SEQ ID NO: 12) |
| 0224 | CGCCGGGTGGTTTCCCGAGGCCTGGTGGTGGTGGTAACG<br>GTGACTTCGAAGAAATCCCGGAAGAGTACCTGTGATAGG<br>ATCAA<br>(SEQ ID NO: 13) |
| 0225 | CTAGTTGATCCTATCACAGGTACTCTTCCGGGATTTCTT<br>CGAAGTCACCGTTACCACCACCACCAGGCCTCGGGAAAC<br>CACCCGGCGGGCT<br>(SEQ ID NO: 14) |
| 0226 | CGCCGAGCCCGCCGAGCCCGCCGGGTGGTTTCGGTCCGA<br>GGCCTGGTGGTGGTAACGGTGACTTCGAAGAAATCC<br>CGGAAGAGTACCTGTGATAGGATCAA<br>(SEQ ID NO: 15) |
| 0227 | CTAGTTGATCCTATCACAGGTACTCTTCCGGGATTTCTT<br>CGAAGTCACCGTTACCACCACCACCAGGCCTCGGACCGA<br>AACCACCCGGCGGGCTCGGCGGGCTCGGCGGGCT<br>(SEQ ID NO: 16) |
| 0265 | CACCCGGCGGAGACGGCGGGCTCAGAGCCAGACCGTTTT<br>CTTCTTTGGTGTGAGAACG<br>(SEQ ID NO: 17) |
| 0281 | CGTCCGGGTGGTGGTGGTAACGGTGACTTCGAAGAAATC<br>CCGGAAGAATACCTGTAAG<br>(SEQ ID NO: 18) |
| 0282 | GATCCGTTCTCACACCAAAGAAGAAAACGGTCTGGCTCT<br>GAGCCCGCCGTCTCCGCCGGGTGGTTTCCCG<br>(SEQ ID NO: 19) |
| 0283 | CTAGCTTACAGGTATTCTTCCGGGATTTCTTCGAAGTCA<br>CCGTTACCACCACCACCCGGACGCGGGAAAC<br>(SEQ ID NO: 20) |
| 0329 | AAGAAATCCCGGAAGAATACCTGCAATAAG<br>(SEQ ID NO: 21) |
| 0330 | CGGTTAAGGCTTGGGGACCGCGGCCGCTGGGTGGTGGTG<br>GTAACGGTGACTTCG<br>(SEQ ID NO: 22) |
| 0331 | ACCACCACCCAGCGGCCGCGGTCCCCAAGCCTTAACCGG<br>GCT<br>(SEQ ID NO: 23) |
| 0332 | CTAGCTTATTGCAGGTATTCTTCCGGGATTTCTTCGAAG<br>TCACCGTTACC<br>(SEQ ID NO: 24) |
| 0333 | CGGTTAAGGCTTTCGGACCGC<br>(SEQ ID NO: 25) |
| 0334 | GGCCGCGGTCCGAAAGCCTTAACCGGGCT<br>(SEQ ID NO: 26) |
| 0335 | CGGTTCGGGCTTTCGGTCCGC<br>(SEQ ID NO: 27) |
| 0336 | GGCCGCGGGACCGAAAGCCCGAACCGGGCT<br>(SEQ ID NO: 28) |
| 0337 | CGGTTAAGGCTTACGGACCGC<br>(SEQ ID NO: 29) |
| 0338 | GGCCGCGGTCCGTAAGCCTTAACCGGGCT<br>(SEQ ID NO: 30) |
| 0339 | CGGTTGTTGCTTTCGGTCCGC<br>(SEQ ID NO: 31) |
| 0340 | GGCCGCGGACCGAAAGCAACAACCGGGCT<br>(SEQ ID NO: 32) |
| 0341 | CGGTTCGGGCTTTCCCGC<br>(SEQ ID NO: 33) |
| 0342 | GGCCGCGGGAAAGCCCGAACCGGGCT |

TABLE 1-continued

| Oligo Code | Oligo Sequence (from 5' to 3') |
|---|---|
| | (SEQ ID NO: 34) |
| 0343 | CGGTTAAGGCTTACCCGC<br>(SEQ ID NO: 35) |
| 0344 | GGCCGCGGGTAAGCCTTAACCGGGCT<br>(SEQ ID NO: 36) |
| 0347 | CGGTTGTTGCTTTCCCGC<br>(SEQ ID NO: 37) |
| 0348 | GGCCGCGGGAAAGCAACAACCGGGCT<br>(SEQ ID NO: 38) |
| 0381 | CGGTTAAGGCTTGGCCGC<br>(SEQ ID NO: 39) |
| 0383 | GGCCGCGGCCAAGCCTTAACCGGGCT<br>(SEQ ID NO: 40) |
| 0384 | CGGTTAAGGCTTTCCCGC<br>(SEQ ID NO: 41) |
| 0385 | GGCCGCGGGAAAGCCTTAACCGGGCT<br>(SEQ ID NO: 42) |
| 0386 | CGGTTGTAGTTTTCCCGC<br>(SEQ ID NO: 43) |
| 0387 | CGGTTGAAGTTTTCCCGC<br>(SEQ ID NO: 44) |
| 0388 | GGCCGCACTACAACTACAACCGGGCT<br>(SEQ ID NO: 45) |
| 0389 | CGGTTGTAGTTGTAGTGC<br>(SEQ ID NO: 46) |
| 0390 | GGCCGCGGGAAAACTTCAACCGGGCT<br>(SEQ ID NO: 47) |
| 0391 | GGCCGCGGGAAAACTACAACCGGGCT<br>(SEQ ID NO: 48) |
| 0392 | CTAGCTTATTCGTTTTTTTCTTCGTCTTCCCAGAACGGT<br>TCGTATTTGTCGTTCGGGTTCCGCAGCAGGAAC<br>(SEQ ID NO: 49) |
| 0393 | GGCCGTTCCTGCTGCGGAACCCGAACGACAAATACGAAC<br>CGTTCTGGGAAGACGAAGAAAAAAACGAATAAG<br>(SEQ ID NO: 50) |
| 0453 | TGGTTAAAGCTTTCCCGC<br>(SEQ ID NO: 51) |
| 0454 | GGCCGCGGGAAAGCTTTAACCAGGCT<br>(SEQ ID NO: 52) |
| 0455 | TGGTTGTTGCTTTCCCGC<br>(SEQ ID NO: 53) |
| 0456 | GGCCGCGGGAAAGCAACAACCAGGCT<br>(SEQ ID NO: 54) |
| 0465 | GGCCGCGGGAACAGAGCCAGACCGTTTTCTTCTTTGGTG<br>TGAGAACG<br>(SEQ ID NO: 55) |
| 0466 | GATCCGTTCTCACACCAAAGAAGAAAACGGTCTGGCTCT<br>GTTCCCGC<br>(SEQ ID NO: 56) |
| 0467 | CGGTTAAGGCTTTCCCGCGGCCGTTCCTGCTGCGGAAC<br>(SEQ ID NO: 57) |
| 0468 | TTTGTCGTTCGGGTTCCGCAGCAGGAACGGCCGCGGGAA<br>AGCCTTAACCGGGCT<br>(SEQ ID NO: 58) |
| 0469 | CTAGCTTATTCGTTTTTTTCTTCGTCTTCCCAGAACGGT<br>TCGTA<br>(SEQ ID NO: 59) |
| 0470 | CCGAACGACAAATACGAACCGTTCTGGGAAGACGAAGAA<br>AAAAACGAATAAG<br>(SEQ ID NO: 60) |

The oligonucleotides were prepared from β-cyanoethyl protected diisopropylamine phosphoamidates in detritylated form in amounts of 0.1 μmole using a synthesizer of Applied Biosystems (Weiterstadt, Model 391) following the manufacturers recommendations. Double-stranded DNA molecules were prepared by converting 100 pmole of two complementary oligonucleotides, dissolved in 50 mM of tri-(hydroxymethyl)aminomethane/HCl (Tris/HCl), 10 mM of magnesium chloride and 5 mM dithiothreitol at pH 7.5 to their phosphorylated forms with one unit of T4-kinase in the presence of 10 mM of adenosine triphosphate, and subsequently converted to double-stranded DNA in the same buffer. The synthetic double-stranded DNA molecules were purified by electrophoresis on a 5% polyacrylamide gel, and then used for ligation with the appropriately prepared plasmid. The plasmids were prepared by digesting with restriction enzymes, isolating the restriction fragment, dephosphorylating the 5'-end, subsequently ligating and then used for transforming *E.coli* K12 JM103. These, as well as all other gene technological experiments, were performed by conventional methods which are described in Sambrook et al. "Molecular Cloning: A Laboratory Manual", 2nd Edition, Cold Spring Harbor Laboratory Press, Cold Spring Harbor, USA, (1989).

b) Preparation of permanent cultures, and fermentation

The recombinant expression plasmids pSJ69, pSJ76, pSJ77, pSJ78, pSJ79, pSJ81, pSJ83, pSJ90, pSJ91, pSJ92, pSJ93, pSJ94, pSJ95, pSJ101, pSJ102, pSJ103, pSJ104, pSJ105, psJ106, pSJ109, pSJ11, pSJ114 and pSJ113 were incorporated into *E.coli* K12 JM103 (ATCC 39403) and plated onto standard-I nutrient agar containing 150 mg/l of ampicillin (Sambrook et al: "Molecular Cloning: A Laboratory Manual"). Individual colonies from each transformation were cultivated to an optical density at 578 nm (OD) of 1 using standard-I nutrient broth (pH 7.0; 150 mg/l of ampicillin) at 200° C. Such cultures were subsequently deep-frozen in liquid nitrogen after addition of dimethylsulfoxide (DMSO) to a final concentration of 7.5% and splitting into five portions of each 2 ml. These portions, the permanent cultures, were then stored at −70° C. For the preparation of the bifunctional urokinase variants, 1 ml of the appropriate permanent culture was suspended in 20 ml standard-I nutrient broth (pH 7.0; 150 mg/l of ampicillin), and cultivated at 37° C. to an OD of 1.

Such cultures were then transferred completely to 1 l standard-I nutrient broth (pH 7.0; 150 mg/l of ampicillin) and fermented in shaker flasks at 37° C. Induction was caused by addition of 2 ml of a solution of indole-3-acrylic acid (60 mg in 2 ml ethanol) after the culture had reached an OD of between 0.5–1.0.

c) Tests of the expression

In order to test the extent of expression, aliquots of cells equivalent to 1 ml of a culture with an OD of 1.0 were removed immediately prior to induction, and thereafter every hour for six hours after induction. The cells were pelleted by centrifuging and then disintegrated by treatment with lysozyme (1 mg/ml of lysozyme in 50 mM of Tris/HCl buffer, pH containing 50 mM of ethylene-diamine tetra-acetic acid (EDTA) and 15% of saccharose). The lysed cells were dissolved in 4–5M of guanidinium hydrochloride, and the resulting solubilized product was then allowed to refold for 2–5 hours after dilution to 1.2M guanidinium hydrochloride and addition of a reducing agent (glutathione or cysteine) (Winkler et al., Biochemistry 25, 4041–4045 (1986)). The single-chain bifunctional urokinase variants which were formed could be determined after cleavage with plasmin to the corresponding enzymatically active two-chain form, and measuring the ability of this form to cleave the chromogenic substrate pyro-Glu-Gly-Arg-p-nitroanilide. Activation of the bifunctional urokinase variants according to the invention was caused by treatment with plasmin in a buffer containing 50 mM of Tris/HCl, 12 mM of sodium chloride and 0.02% of Tween 80 at pH 7.4 and 37° C. The ratio of bifunctional urokinase variant to plasmin was roughly 100–1500 : 1 as a molar ratio or 8.000 to 36.000 : 1 as a ratio of enzyme units. The chromogenic assay was performed in a buffer containing 50 mM of Tris/HCl, 38 mM of sodium chloride, 36 µM of aprotinin (to inhibit plasmin), and 0.27 mM of the substrate pyro-Glu-Gly-Arg-p-nitroanilide at pH 8.8 and 37° C. Depending on the concentration of bifunctional urokinase variant in the assay, the reaction was stopped after 5–60 minutes by addition of an aqueous solution containing 50% by weight of acetic acid, and the extinction measured at 405 nm. According to the information provided by the manufacturer of the substrate (Kabi Vitrum, Sweden), under these conditions a rate of change of the extinction at 405 nm of 0.05 per minute is equivalent to an urokinase activity of 25 Ploug units per ml test solution. The bifunctional urokinase variants according to the invention possess specific activities between 120.000 to 155.000 Ploug units per mg purified protein. The protein content of the test solution was determined with the BCA assay (Pierce).

d) Isolation and purification

Fermentations conducted according to the method described in 1b) were completed 5 to 6 hours after the induction at which time the OD was between 5 and 6. The cells were recovered by centrifuging, resuspended in 200 ml of water and broken in a high-pressure homogenizer. The solids were recovered by centrifugation, and the pellet, which contains all of the bifunctional urokinase variant produced by the cells, was dissolved in 500 ml of 5M guanidinium hydrochloride, 40 mM cysteine and 1 mM EDTA at pH 8. This solution was then diluted with 2000 ml of 25 mM Tris/HCl pH 9.0 to start the refolding process which was completed after ca 12 hours.

The bifunctional urokinase variants which were formed were bound by stirring the refolding solution with 8 g of silica gel for 2 hours. The silica gel was subsequently recovered after settling, and washed with an acetate buffer (pH 4.0). The urokinase variants were then eluted with a buffer containing 0.5M tetramethylammonium chloride (TMAC) in 0.1M acetate buffer (pH 4). After two further chromatographic steps involving a chelate matrix and a cation exchanger, the urokinase variants were obtained in a purified form. Analysis by N-terminal sequencing demonstrated that the variants were single-chain molecules with the required amino terminal sequence. The protein-chemical characterization of the modified carboxyl-terminal region of the individual variants was made possible by cleaving the protein with CNBr in a mixture containing 1 ml of 90% formic acid and 1 ml heptafluorobutyric acid. Under these conditions, cleavage occurs after tryptophan residues. The carboxyl-terminal peptide was purified by high pressure liquid chromatography (HPLC), and then subjected to N-terminal sequencing All of the isolated bifunctional urokinase variants listed in Table 2 showed either no activity, or only a minimal activity, when tested directly in the activity assay using the chromogenic substrate for urokinase.

Only after cleavage with plasmin (as described in Section 1c) could the expected enzymatic activity be measured, ie. 120,000 to 155,000 Ploug units per mg purified protein. Consequently all of the bifunctional urokinase variants were expressed in *E.coli* K12 JM 103 as single-chain proteins.

TABLE 2

Bifunctional urokinase variants (bU) according to the invention having the general formula I, M4—$X_1$—$Y_1$

| bU | $X_1$ | $Y_1$ |
|---|---|---|
| M11 | Ser—Pro—Pro—Ser—Pro—Pro—Gly—Gly—Phe (SEQ ID NO: 61) | $A^{1)}$ with $Y_2$ = Pro, $Y_3$ = peptide bond, $Y_4$ = OH |
| M12 | Ser—Pro—Val—Lys—Ala—Phe (SEQ ID NO: 62) | $A^{1)}$ with $Y_2$ = Pro, $Y_3$ = peptide bond, $Y_4$ = OH |
| M13 | Ser—Pro—Pro—Ser—Pro—Pro—Ser—Pro—Pro—Gly—Gly—Phe (SEQ ID NO: 63) | $A^{1)}$ with $Y_2$ = Pro, $Y_3$ = peptide bond, $Y_4$ = OH |
| M14 | Ser—Pro—Pro—Gly—Gly—Phe (SEQ ID NO: 64) | $A^{1)}$ with $Y_2$ = Pro, $Y_3$ = peptide bond, $Y_4$ = OH |
| M15 | Ser—Pro—Pro—Ser—Pro—Pro—Ser—Pro—Pro—Gly—Gly—Phe—Gly (SEQ ID NO: 65) | $A^{1)}$ with $Y_2$ = Pro, $Y_3$ = peptide bond, $Y_4$ = OH |
| M16 | Ser—Pro—Val—Lys—Ala—Trp—Gly (SEQ ID NO: 66) | $A^{1)}$ with $Y_2$ = Pro, $Y_3$ = Leu, $Y_4$ = Gln |
| M17 | Ser—Pro—Val—Lys—Ala—Phe—Gly (SEQ ID NO: 67) | $A^{1)}$ with $Y_2$ = Pro, $Y_3$ = Leu, $Y_4$ = Gln |
| M18 | Ser—Pro—Val—Arg—Ala—Phe—Gly (SEQ ID NO: 68) | $A^{1)}$ with $Y_2$ = Pro, $Y_3$ = Leu, $Y_4$ = Gln |
| M19 | Ser—Pro—Val—Lys—Ala—Tyr—Gly (SEQ ID NO: 69) | $A^{1)}$ with $Y_2$ = Pro, $Y_3$ = Leu, $Y_4$ = Gln |
| M20 | Ser—Pro—Val—Val—Ala—Phe—Gly (SEQ ID NO: 70) | $A^{1)}$ with $Y_2$ = Pro, $Y_3$ = Leu, $Y_4$ = Gln |
| M21 | Ser—Pro—Val—Arg—Ala—Phe (SEQ ID NO: 71) | $A^{1)}$ with $Y_2$ = Pro, $Y_3$ = Leu, $Y_4$ = Gln |
| M22 | Ser—Pro—Val—Lys—Ala—Tyr (SEQ ID NO: 72) | $A^{1)}$ with $Y_2$ = Pro, $Y_3$ = Leu, $Y_4$ = Gln |
| M23 | Ser—Pro—Val—Val—Ala—Phe (SEQ ID NO: 73) | $A^{1)}$ with $Y_2$ = Pro, $Y_3$ = Leu, $Y_4$ = Gln |
| M24 | Ser—Pro—Val—Lys—Ala—Trp (SEQ ID NO: 74) | $A^{1)}$ with $Y_2$ = Pro, $Y_3$ = Leu, $Y_4$ = Gln |
| M25 | Ser—Pro—Val—Lys—Ala—Phe (SEQ ID NO: 75) | $A^{1)}$ with $Y_2$ = Pro, $Y_3$ = Leu, $Y_4$ = Gln |
| M26 | Ser—Pro—Val—Val—Val—Phe (SEQ ID NO: 76) | $A^{1)}$ with $Y_2$ = Pro, $Y_3$ = Leu, $Y_4$ = Gln |
| M27 | Ser—Pro—Val—Glu—Val—Phe (SEQ ID NO: 77) | $A^{1)}$ with $Y_2$ = Pro, $Y_3$ = Leu, $Y_4$ = Gln |
| M28 | Ser—Pro—Val—Val—Val—Val (SEQ ID NO: 78) | $A^{1)}$ with $Y_2$ = Val, $Y_3$ = Leu, $Y_4$ = Gln |
| M29 | Ser—Pro—Val—Val—Ala—Phe (SEQ ID NO: 79) | $B^{2)}$ with $Y_2$ = Pro |
| M30 | Ser—Leu—Val—Val—Ala—Phe (SEQ ID NO: 80) | $A^{1)}$ with $Y_2$ = Pro, $Y_3$ = Leu, $Y_4$ = Gln |
| M31 | Ser—Leu—Val—Lys—Ala—Phe (SEQ ID NO: 81) | $A^{1)}$ with $Y_2$ = Pro, $Y_3$ = Leu, $Y_4$ = Gln |
| M32 | Ser—Pro—Val—Lys—Ala—Phe (SEQ ID NO: 82) | $B^{2)}$ with $Y_2$ = Pro |
| M33 | peptide bond | $A^{1)}$ with $Y_2$ = Pro, $Y_3$ = Leu, $Y_4$ = Gln |

$^{1)}$A = $Y_2$—Arg—Pro—$Y_3$—Gly—Gly—Gly—Gly—Asn—Gly—Asp—Phe—Glu—Glu—Ile—Pro—Glu—Glu—Tyr—Leu—$Y_4$ (SEQ ID NO: 4)
$^{2)}$B = $Y_2$—Arg—Pro—Phe—Leu—Leu—Arg—Asn—Pro—Asn—Asp—Lys—Tyr—Glu—Pro—Phe—Trp—Glu—Asp—Glu—Glu—Lys—Asn—Glu (SEQ ID NO: 5)

2) Pharmacological Investigations

Measurement of the thrombin inhibitory activity

Figure 3:
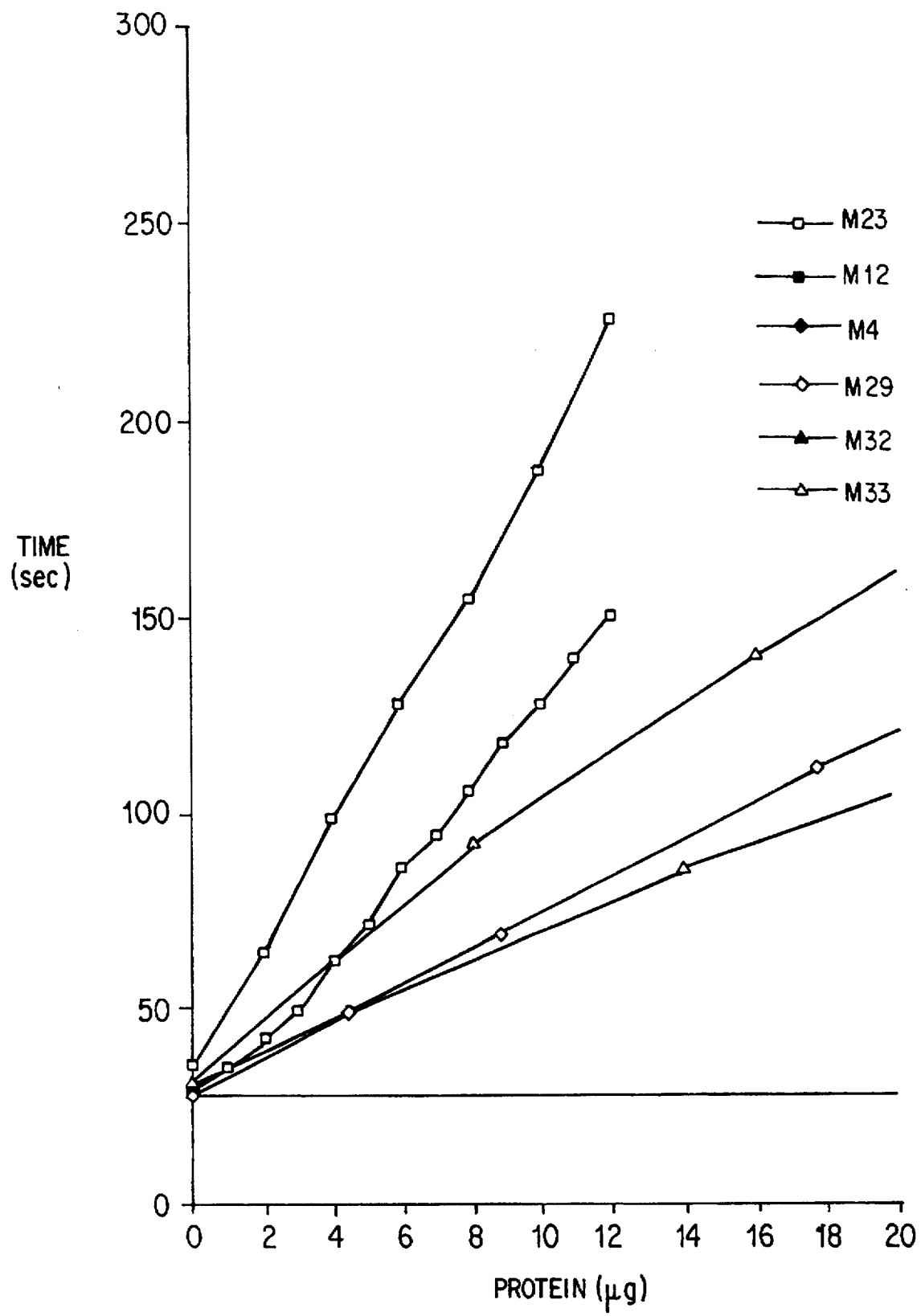

The inhibitor activities of the bifunctional urokinase variants according to the invention were determined by measuring the thrombin time. For this, 200 μl of a 10-fold dilution of human citrate plasma with veronal buffer were mixed with 50 μl thrombin solution (0.2 Units) and 50 μl of an aqueous solution containing 0.5 to 50 μg of one of the bifunctional urokinase variants. The time required for the formation of a fibrin network was then measured. The measured inhibitory factors are presented in Table 3, and are the factors by which the thrombin time was increased in the presence of 10 μg of each of the bifunctional urokinase variants according to the invention. The concentration dependent increases in the thrombin times were also determined, and those of the bifunctional urokinase variants M12, M23, M29, M32, M33 are presented graphically in relation to M4 in FIG. 3. In contrast to the bifunctional urokinase variants according to the invention, the time required for clotting was increased neither by M4, i.e. the protein with the amino acid sequence $Ser^{47}$ to $Leu^{411}$ of unglycosylated prourokinase shown in FIG. 1, nor by unglycosylated prourokinase (Saruplase), nor by LUK in doses of up to 1 mg.

TABLE 3

Increases in the thrombin time caused by the bifunctional urokinase variants according to the invention having the general formula I, M4—$X_1$—$Y_1$

| Bifunctional Urokinase Variant | Inhibitory Factor[1) |
|---|---|
| M11 | 1.8 |
| M12 | 4.6 |
| M13 | 1.7 |
| M14 | 1.8 |
| M15 | 2.5 |

TABLE 3-continued

Increases in the thrombin time caused by the bifunctional urokinase variants according to the invention having the general formula I, M4—X₁—Y₁

| Bifunctional Urokinase Variant | Inhibitory Factor[1] |
|---|---|
| M16 | 3.2 |
| M17 | 3.1 |
| M18 | 2.9 |
| M19 | 2.0 |
| M20 | 2.2 |
| M21 | 2.3 |
| M22 | 3.7 |
| M23 | 5.3 |
| M24 | 6.2 |
| M25 | 2.9 |
| M26 | 3.2 |
| M27 | 2.0 |
| M28 | 2.1 |
| M29 | 2.6 |
| M30 | 3.4 |
| M31 | 2.0 |
| M32 | 3.0 |
| M33 | 2.0 |

[1] Measured for the effect of 10 µg protein. The inhibitory factor is the quotient of the thrombin time in the presence of one of the inhibitors, and the thrombin time in the absence of an inhibitor.

Pharmacological properties of the bifunctional urokinase variants M12 and M23 in an animal model In a pharmacological in vivo model the effects of the bifunctional urokinase variants M12 and M23 on lysis of arterial occlusive thrombi were compared to the effects of saruplase (unglycosylated prourokinase). In anesthetized rabbits, a completely occlusive thrombus was induced in a temporarily isolated segment of about 1 cm in length of the femoral artery by local injection of thrombin and $^{125}$I-labeled human fibrinogen via a side branch of the artery. The size of the formed thrombus was measured as the incorporated radioactivity of the human fibrin by using an extracorporal gamma-detector. Electromagnetic measurement of blood flow and detection of thrombus radioactivity were performed continuously for the entire experimental period. Fibrinolytic effects were thus quantified as reperfusion of occluded blood vessels as well as degradation of the radioactively labeled incorporated thrombus fibrin. Blood samples were collected before administration as well as 30, 60 and 90 minutes after administration of the bifunctional urokinase variants according to the invention; in these blood samples plasma concentrations of fibrinogen were determined. 6 mg/kg each of M12, M23 and saruplase were administered as intravenous bolus injection. Because M12 and M23 in contrast to saruplase possess an additional anti-coagulatory effect, an experimental group was included in which saruplase was combined with the anticoagulant heparin (150 U/kg i.v.-bolus). Group size in each case was 6 animals.

During the 90 minute experimental period, thrombolysis of the labeled thrombus fibrin was 46±11% for M12, 43±12% for M23, 22±5% for saruplase and 39±15% for the saruplase-heparin-combination. Bolus applications of M12 and M23 induced recanalization of the thrombotically occluded artery in all animals (6 animals in each case); by application of saruplase in 5 out of 6 animals and by application of saruplase plus heparin in 4 out of 6 animals the obstructed vessel could be recanalized. The maximum reperfusion blood flow (in % of prethrombotic baseline value) amounted to 95±10% for M12 and 82±9% for M23; both values were significantly different from the maximum height of reperfusion blood flow of 43±12% achieved by saruplase. The maximum reperfusion blood flow due to treatment with saruplase plus heparin was 58±8% and thus was between the results for M12 and M23 on the one side and saruplase on the other side; there was no significant difference towards both sides. The total fibrinolytic effect was calculated as area of the reperfusion blood flow (as % of initial values) over the 90 minutes of the experimental period. This total effect was 4,502±1,127%×min for M12 and 4,270±885%×min for M23; for both urokinase variants according to the invention the effect was significantly greater than the effect of 1,519±643%×min that was achieved by saruplase. The combined treatment of saruplase plus heparin resulted in a total effect of 2,217±761%×min; this effect was not significantly better than the effect by treatment with saruplase alone and was clearly lower than the results achieved by M12 and M23. The results are summarized in table 4.

TABLE 4

Thrombolytic effect after i.v.-bolus application; femoral artery thrombosis, anesthetized rabbit.

| Polypeptide | Dose | % $^{125}$I Fibrinolysis | Maximum Reperfusion Flow (% of pre-value) | Cumulative Reperfusion Flow (% × min.) |
|---|---|---|---|---|
| M12 | 6 mg/kg | 46 ± 11 | 95 ± 10* | 4502 ± 1127 |
| M23 | 6 mg/kg | 43 ± 12 | 82 ± 9* | 4270 ± 885* |
| Saruplase | 6 mg/kg | 22 ± 5 | 43 ± 12 | 1519 ± 643 |
| Saruplase + Heparin | 6 mg/kg 150 mg/kg | 39 ± 15 | 58 ± 8 | 2217 ± 761 |

* p < 0.05 vs Saruplase

Surprisingly it has been found that after bolus application of M12 as well as after bolus application of M23 there were significantly lower decreases of the plasma concentrations of fibrinogen than after bolus application of saruplase. The results are summarized in table 5.

TABLE 5

Effect of bolus applications of M12 and M23 compared to saruplase, with and without heparin, on the decrease of the plasma fibrinogen concentration; anesthetized rabbit.

| Polypeptide | Dose | Decrease of plasma fibrinogen (% change verses baseline value) Time after administration | | |
|---|---|---|---|---|
| | | 30 min. | 60 min. | 90 min. |
| M12 | 6 mg/kg | −19 ± 9 | −20 ± 9* | −19 ± 9* |
| M23 | 6 mg/kg | −20 ± 11* | −21 ± 11* | −20 ± 11* |
| Saruplase | 6 mg/kg | −64 ± 7 | −66 ± 6 | −67 ± 6 |
| Saruplase + Heparin | 6 mg/kg + 150 mg/kg | n.d.[1] | −46 ± 8 | −45 ± 9 |

*p < 0.05 vs Saruplase
[1] n.d. = not determined

The results demonstrate that the bifunctional urokinase variants according to the invention M12 and M23 dissolve total occlusive arterial thrombi and restore the blood flow through the thrombosed vessels. This effect was achieved by a single bolus injection of M12 and M23, respectively, in non-heparinized animals. These thrombolytic effects of M12 and M23 were not only more pronounced than the effect of saruplase, but surprisingly they were also associated with a lower consumption of plasma fibrinogen. This means that M12 and M23 possess a significantly higher fibrin specificity than saruplase. The better preservation of plasma fibrinogen by M12 and M23 compared to saruplase means that the coagulability of the blood is better maintained; thereby the risk of uncontrolled bleeding as a possible complication of a systemic fibrinogen degradation is reduced. Thus, M12 and M23 have to be estimated as safer compounds than saruplase with regard to hemostaseological side effects.

---

We claim:

1. A plasmid for use in producing a bifunctional urokinase variant corresponding to the formula I

M4-X₁—Y₁ wherein

M4 represents the amino acid sequence from ⁴⁷Ser to ⁴¹¹Leu of the unglycosylated prourokinase as set forth in SEQ ID NO:83.

X₁ represents a peptide bond, or
a peptide sequence selected from the group consisting of
Ser-Pro-Pro-Ser-Pro-Pro-Gly-Gly-Phe (SEQ ID NO:1),
Ser-Pro-Pro-Ser-Pro-Pro-Ser-Pro-Pro-Gly-Gly-Phe (SEQ ID NO:2), and
Ser-Pro-Pro-Ser-Pro-Pro-Ser-Pro-Pro-Gly-Gly-Phe-Gly (SEQ ID NO:3),
or a peptide sequence of formula II Ser-X₂-X₃-X₄-X₅-X₆-X₇ wherein X₂ is Pro or Leu, X₃ is Val or Pro, X₄ is Lys, Val, Arg, Gly or Glu, X₅ is Ala, Val, Gly, Leu or Ile, X₆ is Phe, Trp, Tyr or Val and X₇ is a peptide bond or Gly, and Y₁ represents a peptide sequence selected from the group consisting of
Y₂-Arg-Pro-Y₃-Gly-Gly-Gly-Gly-Asn-Gly-Asp-Phe-Glu-Glu-Ile-Pro-Glu-Glu-Tyr-Leu-Y₄ (SEQ ID NO:4),
Y₂-Arg-Pro-Phe-Leu-Leu-Arg-Asn-Pro-Asn-Asp-Lys-Tyr-Glu-Pro-Phe-Trp-Glu-Asp-Glu-Glu-Lys-Asn-Glu (SEQ ID NO:5), and
Y₂-Arg-Pro-Ser-Ser-Glu-Phe-Glu-Glu-Phe-Glu-Ile-Asp-Glu-Glu-Glu-Lys (SEQ ID NO:6)

wherein Y₂ is Pro or Val, Y₃ is Leu or a peptide bond, and Y₄ is Gln or a hydroxyl group; said plasmid comprising an operon which comprises a regulatable promotor, a Shine-Dalgarno sequence effective as ribosomal binding site, a start codon, a synthetic structural gene for the bifunctional urokinase variant, and downstream of said structural gene, at least one terminator; and said plasmid being suitable for expressing said bifunctional urokinase variant in strains of *Escherichia coli*.

2. A plasmid according to claim 1, wherein said Shine-Dalgarno sequence is spaced 6 to 12 nucleotides from said start codon.

3. A plasmid according to claim 2, wherein said Shine-Dalgarno sequence is spaced 8 to 10 nucleotides from said start codon.

4. A plasmid according to claim 1, selected from the group consisting of pSJ 69, pSJ 76, pSJ 77, pSJ 78, pSJ 79, pSJ 81, pSJ 83, pSJ 90, pSJ 91, pSJ 92, pSJ 93, pSJ 94, pSJ 95, pSJ 101, pSJ 102, pSJ 103, pSJ 104, pSJ 105, pSJ 106, pSJ 109, pSJ 111, pSJ 114, and pSJ 113.

5. A plasmid according to claim 4, selected from the group consisting of pSJ 76, pSJ 81, pSJ 83, pSJ 90, pSJ 91, pSJ 92, pSJ 93, pSJ 94, pSJ 95, pSJ 101, pSJ 102, pSJ 103, pSJ 105, pSJ 106, pSJ 109, pSJ 111, and pSJ 114.

6. A plasmid according to claim 4, selected from the group consisting of pSJ 76, pSJ 81, pSJ 83, pSJ 91, pSJ 92, pSJ 94, pSJ 95, pSJ 101, pSJ 102, pSJ 103, pSJ 106, pSJ 109, pSJ 111, and pSJ 114.

7. A plasmid according to claim 4, selected from the group consisting of pSJ 76, pSJ 94, pSJ 95, pSJ 101, pSJ 102, pSJ 103, pSJ 106, pSJ 109, pSJ 111, and pSJ 114.

8. A process for producing a plasmid according to claim 1, wherein the plasmid is constructed from the plasmids pBlueskript KS II+, pUC 8 and pGR 201 according to FIGS. 2 and 2a to 2p.

9. A method of producing a bifunctional urokinase variant corresponding to the formula I

M4-X₁—Y₁ wherein

M4 represents the amino acid sequence from ⁴⁷Ser to ⁴¹¹Leu of the unglycosylated prourokinase as set forth in SEQ ID NO:83.

X₁ represents a peptide bond, or
a peptide sequence selected from the group consisting of
Ser-Pro-Pro-Ser-Pro-Pro-Gly-Gly-Phe (SEQ ID NO:1),
Ser-Pro-Pro-Ser-Pro-Pro-Ser-Pro-Pro-Gly-Gly-Phe (SEQ ID NO:2), and
Ser-Pro-Pro-Ser-Pro-Pro-Ser-Pro-Pro-Gly-Gly-Phe-Gly (SEQ ID NO:3),
or a peptide sequence of formula II Ser-X$_2$-X$_3$-X$_4$-X$_5$-X$_6$-X$_7$ wherein X$_2$ is Pro or Leu, X$_3$ is Val or Pro, X$_4$ is Lys, Val, Arg, Gly or Glu, X$_5$ is Ala, Val, Gly, Leu or Ile, X$_6$ is Phe, Trp, Tyr or Val and X$_7$ is a peptide bond or Gly, and Y$_1$ represents a peptide sequence selected from the group consisting of Y$_2$-Arg-Pro-Y$_3$-Gly-Gly-Gly-Gly-Asn-Gly-Asp-Phe-Glu-Glu-Ile-Pro-Glu-Glu-Tyr-Leu-Y$_4$ (SEQ ID NO:4), Y$_2$-Arg-Pro-Phe-Leu-Leu-Arg-Asn-Pro-Asn-Asp-Lys-Tyr-Glu-Pro-Phe-Trp-Glu-Asp-Glu-Glu-Lys-Asn-Glu (SEQ ID NO:5), and Y$_2$-Arg-Pro-Ser-Ser-Glu-Phe-Glu-Glu-Phe-Glu-Ile-Asp-Glu-Glu-Glu-Lys (SEQ ID NO:6)

wherein Y$_2$ is Pro or Val, Y$_3$ is Leu or a peptide bond, and

Y$_4$ is Gln or a hydroxyl group;

said method comprising the steps of:

transforming a strain of *Escherichia coli* with a plasmid comprising an operon which comprises a regulatable promotor, a Shine-Dalgarno sequence effective as ribosomal binding site, a start codon, a synthetic structural gene for the bifunctional urokinase variant, and downstream of said structural gene, at least one terminator; and said plasmid being suitable for expressing said bifunctional urokinase variant in strains of *Escherichia coli*;

culturing said transformed *Escherichia coli* in a medium and inducing expression of said structural gene whereby an inactive intermediate protein of said bifunctional urokinase variant is expressed into said medium;

lysing cells of said *Escherichia coli*;

isolating said inactive intermediate protein from said medium;

solubilizing the intermediate protein, and refolding the solubilized intermediate protein by means of a redox system, whereby a polypeptide of formula I is obtained.

* * * * *

SEQUENCE LISTING ( 1 ) GENERAL INFORMATION:

( i i i ) NUMBER OF SEQUENCES: 83

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:1:

Ser Pro Pro Ser Pro Pro Gly Gly Phe
    1                  5

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:2:

Ser Pro Pro Ser Pro Pro Ser Pro Pro Gly Gly Phe
    1                  5                            10

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:3:

Ser Pro Pro Ser Pro Pro Ser Pro Pro Gly Gly Phe Gly
    1                  5                            10

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /note="Xaa at position 1
            represents Pro or Val"

( i x ) FEATURE:
        ( A ) NAME/KEY: Modified-site
        ( B ) LOCATION: 4
        ( D ) OTHER INFORMATION: /note="Xaa at position 4
            represents Leu or a peptide bond"

( i x ) FEATURE:
        ( A ) NAME/KEY: Modified-site
        ( B ) LOCATION: 21
        ( D ) OTHER INFORMATION: /note="Xaa at position 21
            represents Gln or a hydroxyl group"

( x i ) SEQUENCE DESCRIPTION: SEQ ID NO:4:

Xaa Arg Pro Xaa Gly Gly Gly Gly Asn Gly Asp Phe Glu Glu Ile Pro

```
        1               5                   10                  15

Glu  Glu  Tyr  Leu  Xaa
                      20
```

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /note="Xaa at position 1
            represents Pro or Val"

( x i ) SEQUENCE DESCRIPTION: SEQ ID NO:5:

```
     Xaa  Arg  Pro  Phe  Leu  Leu  Arg  Asn  Pro  Asn  Asp  Lys  Tyr  Glu  Pro  Phe
     1                   5                        10                       15

Trp  Glu  Asp  Glu  Glu  Lys  Asn  Glu
                      20
```

( 2 ) INFORMATION FOR SEQ ID NO:6:

( i ) SEQUENCE CHARACTERISTICS:
        ( A ) LENGTH: 17 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /note="Xaa at position 1
            represents Pro or Val"

( x i ) SEQUENCE DESCRIPTION: SEQ ID NO:6:

```
     Xaa  Arg  Pro  Ser  Ser  Glu  Phe  Glu  Glu  Phe  Glu  Ile  Asp  Glu  Glu  Glu
     1                   5                        10                       15

Lys
```

( 2 ) INFORMATION FOR SEQ ID NO:7:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
TATGAGCAAA  ACTTGCTACG  AAGGTAACGG  TCACTTCTAC  CGTGGTAAGG  CTTCTACCGA      60

CAC                                                                         63
```

( 2 ) INFORMATION FOR SEQ ID NO:8:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CATGGTGTCG  GTAGAAGCCT  TACCACGGTA  GAAGTGACCG  TTACCTTCGT  AGCAAGTTTT      60

GCTCA                                                                       65
```

( 2 ) INFORMATION FOR SEQ ID NO:9:

( i ) SEQUENCE CHARACTERISTICS:
    ( A ) LENGTH: 83 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

| | | | | | |
|---|---|---|---|---|---|
| CGGTTAAGGC | TTTCCCGAGG | CCTGGTGGTG | GTGGTAACGG | TGACTTCGAA | GAAATCCCGG | 60
| AAGAGTACCT | GTGATAGGAT | CAA | | | | 83

( 2 ) INFORMATION FOR SEQ ID NO:10:

( i ) SEQUENCE CHARACTERISTICS:
    ( A ) LENGTH: 91 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

| | | | | | |
|---|---|---|---|---|---|
| CTAGTTGATC | CTATCACAGG | TACTCTTCCG | GGATTTCTTC | GAAGTCACCG | TTACCACCAC | 60
| CACCAGGCCT | CGGGAAAGCC | TTAACCGGGC | T | | | 91

( 2 ) INFORMATION FOR SEQ ID NO:11:

( i ) SEQUENCE CHARACTERISTICS:
    ( A ) LENGTH: 101 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CGCCGAGCCC GCCGAGCCCG CCGGGTGGTT TCCCGAGGCC TGGTGGTGGT GGTAACGGTG    60
ACTTCGAAGA AATCCCGGAA GAGTACCTGT GATAGGATCA A    101

( 2 ) INFORMATION FOR SEQ ID NO:12:

( i ) SEQUENCE CHARACTERISTICS:
    ( A ) LENGTH: 109 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

CTAGTTGATC CTATCACAGG TACTCTTCCG GGATTTCTTC GAAGTCACCG TTACCACCAC    60
CACCAGGCCT CGGGAAACCA CCCGGCGGGC TCGGCGGGCT CGGCGGGCT    109

( 2 ) INFORMATION FOR SEQ ID NO:13:

( i ) SEQUENCE CHARACTERISTICS:
    ( A ) LENGTH: 83 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

CGCCGGGTGG TTTCCCGAGG CCTGGTGGTG GTGGTAACGG TGACTTCGAA GAAATCCCGG    60
AAGAGTACCT GTGATAGGAT CAA    83

( 2 ) INFORMATION FOR SEQ ID NO:14:

( i ) SEQUENCE CHARACTERISTICS:
    ( A ) LENGTH: 91 base pairs
    ( B ) TYPE: nucleic acid
    ( C ) STRANDEDNESS: single ( D ) TOPOLOGY: linear ( x i ) SEQUENCE DESCRIPTION: SEQ ID NO:14:

```
CTAGTTGATC CTATCACAGG TACTCTTCCG GGATTTCTTC GAAGTCACCG TTACCACCAC      60
CACCAGGCCT CGGGAAACCA CCCGGCGGGC T                                     91
```

( 2 ) INFORMATION FOR SEQ ID NO:15:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
CGCCGAGCCC GCCGAGCCCG CCGGGTGGTT TCGGTCCGAG GCCTGGTGGT GGTGGTAACG      60
GTGACTTCGA AGAAATCCCG GAAGAGTACC TGTGATAGGA TCAA                      104
```

( 2 ) INFORMATION FOR SEQ ID NO:16:

( i ) SEQUENCE CHARACTERISTICS:
        ( A ) LENGTH: 112 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
CTAGTTGATC CTATCACAGG TACTCTTCCG GGATTTCTTC GAAGTCACCG TTACCACCAC      60
CACCAGGCCT CGGACCGAAA CCACCCGGCG GGCTCGGCGG GCTCGGCGGG CT             112
```

( 2 ) INFORMATION FOR SEQ ID NO:17:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
CACCCGGCGG AGACGGCGGG CTCAGAGCCA GACCGTTTTC TTCTTTGGTG TGAGAACG        58
```

( 2 ) INFORMATION FOR SEQ ID NO:18:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
CGTCCGGGTG GTGGTGGTAA CGGTGACTTC GAAGAAATCC GGAAGAATA CCTGTAAG         58
```

( 2 ) INFORMATION FOR SEQ ID NO:19:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
GATCCGTTCT CACACCAAAG AAGAAAACGG TCTGGCTCTG AGCCCGCCGT CTCCGCCGGG      60
TGGTTTCCCG                                                             70
```

( 2 ) INFORMATION FOR SEQ ID NO:20:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
CTAGCTTACA GGTATTCTTC CGGGATTTCT TCGAAGTCAC CGTTACCACC ACCACCCGGA      60

CGCGGGAAAC                                                             70
```

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
AAGAAATCCC GGAAGAATAC CTGCAATAAG                                       30
```

( 2 ) INFORMATION FOR SEQ ID NO:22:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
CGGTTAAGGC TTGGGGACCG CGGCCGCTGG GTGGTGGTGG TAACGGTGAC TTCG            54
```

( 2 ) INFORMATION FOR SEQ ID NO:23:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
ACCACCACCC AGCGGCCGCG GTCCCCAAGC CTTAACCGGG CT                         42
```

( 2 ) INFORMATION FOR SEQ ID NO:24:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
CTAGCTTATT GCAGGTATTC TTCCGGGATT TCTTCGAAGT CACCGTTACC                 50
```

( 2 ) INFORMATION FOR SEQ ID NO:25:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
CGGTTAAGGC TTTCGGACCG C                                                21
```

( 2 ) INFORMATION FOR SEQ ID NO:26:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

GGCCGCGGTC CGAAAGCCTT AACCGGGCT     29

( 2 ) INFORMATION FOR SEQ ID NO:27:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

CGGTTCGGGC TTTCGGTCCG C     21

( 2 ) INFORMATION FOR SEQ ID NO:28:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

GGCCGCGGAC CGAAAGCCCG AACCGGGCT     29

( 2 ) INFORMATION FOR SEQ ID NO:29:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

CGGTTAAGGC TTACGGACCG C     21

( 2 ) INFORMATION FOR SEQ ID NO:30:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

GGCCGCGGTC CGTAAGCCTT AACCGGGCT     29

( 2 ) INFORMATION FOR SEQ ID NO:31:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

CGGTTGTTGC TTTCGGTCCG C     21

( 2 ) INFORMATION FOR SEQ ID NO:32:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:32:

GGCCGCGGAC CGAAAGCAAC AACCGGGCT 29

( 2 ) INFORMATION FOR SEQ ID NO:33:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:33:

CGGTTCGGGC TTTCCCGC 18

( 2 ) INFORMATION FOR SEQ ID NO:34:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:34:

GGCCGCGGGA AAGCCCGAAC CGGGCT 26

( 2 ) INFORMATION FOR SEQ ID NO:35:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:35:

CGGTTAAGGC TTACCCGC 18

( 2 ) INFORMATION FOR SEQ ID NO:36:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:36:

GGCCGCGGGT AAGCCTTAAC CGGGCT 26

( 2 ) INFORMATION FOR SEQ ID NO:37:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:37:

CGGTTGTTGC TTTCCCGC 18

( 2 ) INFORMATION FOR SEQ ID NO:38:

( i ) SEQUENCE CHARACTERISTICS:
  ( A ) LENGTH: 26 base pairs ( B ) TYPE: nucleic acid
            ( C ) STRANDEDNESS: single
            ( D ) TOPOLOGY: linear ( x i ) SEQUENCE DESCRIPTION: SEQ ID NO:38:

GGCCGCGGGA AAGCAACAAC CGGGCT                    26

( 2 ) INFORMATION FOR SEQ ID NO:39:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:39:

CGGTTAAGGC TTGGCCGC                             18

( 2 ) INFORMATION FOR SEQ ID NO:40:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:40:

GGCCGCGGCC AAGCCTTAAC CGGGCT                    26

( 2 ) INFORMATION FOR SEQ ID NO:41:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:41:

CGGTTAAGGC TTTCCCGC                             18

( 2 ) INFORMATION FOR SEQ ID NO:42:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:42:

GGCCGCGGGA AAGCCTTAAC CGGGCT                    26

( 2 ) INFORMATION FOR SEQ ID NO:43:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:43:

CGGTTGTAGT TTTCCCGC                             18

( 2 ) INFORMATION FOR SEQ ID NO:44:

( i ) SEQUENCE CHARACTERISTICS:
            ( A ) LENGTH: 18 base pairs
            ( B ) TYPE: nucleic acid
            ( C ) STRANDEDNESS: single

```
            ( D ) TOPOLOGY: linear ( x i ) SEQUENCE DESCRIPTION: SEQ ID NO:44:

CGGTTGAAGT TTTCCCGC                                                              1 8

( 2 ) INFORMATION FOR SEQ ID NO:45:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:45:

GGCCGCACTA CAACTACAAC CGGGCT                                                     2 6

( 2 ) INFORMATION FOR SEQ ID NO:46:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:46:

CGGTTGTAGT TGTAGTGC                                                              1 8

( 2 ) INFORMATION FOR SEQ ID NO:47:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:47:

GGCCGCGGGA AAACTTCAAC CGGGCT                                                     2 6

( 2 ) INFORMATION FOR SEQ ID NO:48:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:48:

GGCCGCGGGA AAACTACAAC CGGGCT                                                     2 6

( 2 ) INFORMATION FOR SEQ ID NO:49:

( i ) SEQUENCE CHARACTERISTICS:
            ( A ) LENGTH: 72 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:49:

CTAGCTTATT CGTTTTTTC TTCGTCTTCC CAGAACGGTT CGTATTTGTC GTTCGGGTTC                 6 0

CGCAGCAGGA AC                                                                    7 2

( 2 ) INFORMATION FOR SEQ ID NO:50:

( i ) SEQUENCE CHARACTERISTICS:
            ( A ) LENGTH: 72 base pairs
            ( B ) TYPE: nucleic acid
            ( C ) STRANDEDNESS: single
```

( D ) TOPOLOGY: linear ( x i ) SEQUENCE DESCRIPTION: SEQ ID NO:50:

GGCCGTTCCT GCTGCGGAAC CCGAACGACA AATACGAACC GTTCTGGGAA GACGAAGAAA  60

AAAACGAATA AG  72

( 2 ) INFORMATION FOR SEQ ID NO:51:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

TGGTTAAAGC TTTCCCGC  18

( 2 ) INFORMATION FOR SEQ ID NO:52:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GGCCGCGGGA AAGCTTTAAC CAGGCT  26

( 2 ) INFORMATION FOR SEQ ID NO:53:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

GGCCGCGGGA AAGCAACAAC CAGGCT  26

( 2 ) INFORMATION FOR SEQ ID NO:54:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

GGCCGCGGGA ACAGAGCCAG ACCGTTTTCT TCTTTGGTGT GAGAACG  47

( 2 ) INFORMATION FOR SEQ ID NO:55:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

GATCCGTTCT CACACCAAAG AAGAAAACGG TCTGGCTCTG TTCCCGC  47

( 2 ) INFORMATION FOR SEQ ID NO:56:

( i ) SEQUENCE CHARACTERISTICS:
        ( A ) LENGTH: 38 base pairs
        ( B ) TYPE: nucleic acid
        ( C ) STRANDEDNESS: single ( D ) TOPOLOGY: linear ( x i ) SEQUENCE DESCRIPTION: SEQ ID NO:56:

CGGTTAAGGC TTTCCCGCGG CCGTTCCTGC TGCGGAAC    38

( 2 ) INFORMATION FOR SEQ ID NO:57:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:57:

TTTGTCGTTC GGGTTCCGCA GCAGGAACGG CCGCGGGAAA GCCTTAACCG GGCT    54

( 2 ) INFORMATION FOR SEQ ID NO:58:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:58:

CTAGCTTATT CGTTTTTTTC TTCGTCTTCC CAGAACGGTT CGTA    44

( 2 ) INFORMATION FOR SEQ ID NO:59:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:59:

CCGAACGACA AATACGAACC GTTCTGGGAA GACGAAGAAA AAAACGAATA AG    52

( 2 ) INFORMATION FOR SEQ ID NO:60:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:60:

Ser Pro Pro Ser Pro Pro Gly Gly Phe
   1               5

( 2 ) INFORMATION FOR SEQ ID NO:61:

( i ) SEQUENCE CHARACTERISTICS:
    ( A ) LENGTH: 6 amino acids
    ( B ) TYPE: amino acid
    ( D ) TOPOLOGY: linear ( x i ) SEQUENCE DESCRIPTION: SEQ ID NO:61:

Ser Pro Val Lys Ala Phe
   1               5

( 2 ) INFORMATION FOR SEQ ID NO:62:

( i ) SEQUENCE CHARACTERISTICS:
    ( A ) LENGTH: 12 amino acids
    ( B ) TYPE: amino acid
    ( D ) TOPOLOGY: linear ( x i ) SEQUENCE DESCRIPTION: SEQ ID NO:62:

```
    Ser  Pro  Pro  Ser  Pro  Pro  Ser  Pro  Pro  Gly  Gly  Phe
    1                  5                        10
```

( 2 ) INFORMATION FOR SEQ ID NO:63:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:63:

```
    Ser  Pro  Pro  Gly  Gly  Phe
    1                  5
```

( 2 ) INFORMATION FOR SEQ ID NO:64:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:64:

```
    Ser  Pro  Pro  Ser  Pro  Pro  Ser  Pro  Pro  Gly  Gly  Phe  Gly
    1                  5                        10
```

( 2 ) INFORMATION FOR SEQ ID NO:65:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:65:

```
    Ser  Pro  Val  Lys  Ala  Trp  Gly
    1                  5
```

( 2 ) INFORMATION FOR SEQ ID NO:66:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:66:

```
    Ser  Pro  Val  Lys  Ala  Phe  Gly
    1                  5
```

( 2 ) INFORMATION FOR SEQ ID NO:67:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:67:

```
    Ser  Pro  Val  Lys  Ala  Phe  Gly
    1                  5
```

( 2 ) INFORMATION FOR SEQ ID NO:68:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:68:

```
    Ser  Pro  Val  Arg  Ala  Phe  Gly
```

(2) INFORMATION FOR SEQ ID NO:69:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:69:

Ser Pro Val Lys Ala Tyr Gly
    1                   5

(2) INFORMATION FOR SEQ ID NO:70:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:70:

Ser Pro Val Val Ala Phe Gly
    1                   5

(2) INFORMATION FOR SEQ ID NO:71:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:71:

Ser Pro Val Arg Ala Phe
    1                 5

(2) INFORMATION FOR SEQ ID NO:72:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:72:

Ser Pro Val Lys Ala Tyr
    1                 5

(2) INFORMATION FOR SEQ ID NO:73:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:73:

Ser Pro Val Val Ala Phe
    1                 5

(2) INFORMATION FOR SEQ ID NO:74:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:74:

Ser Pro Val Lys Ala Trp
    1                 5

( 2 ) INFORMATION FOR SEQ ID NO:75:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:75:

Ser  Pro  Val  Lys  Ala  Phe
  1                    5

( 2 ) INFORMATION FOR SEQ ID NO:76:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:76:

Ser  Pro  Val  Val  Val  Phe
  1                    5

( 2 ) INFORMATION FOR SEQ ID NO:77:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:77:

Ser  Pro  Val  Glu  Val  Phe
  1                    5

( 2 ) INFORMATION FOR SEQ ID NO:78:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:78:

Ser  Pro  Val  Val  Val  Val
  1                    5

( 2 ) INFORMATION FOR SEQ ID NO:79:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:79:

Ser  Pro  Val  Val  Ala  Phe
  1                    5

( 2 ) INFORMATION FOR SEQ ID NO:80:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:80:

Ser  Leu  Val  Val  Ala  Phe
  1                    5

( 2 ) INFORMATION FOR SEQ ID NO:81:

( i ) SEQUENCE CHARACTERISTICS:
     ( A ) LENGTH: 6 amino acids
     ( B ) TYPE: amino acid
     ( D ) TOPOLOGY: linear ( x i ) SEQUENCE DESCRIPTION: SEQ ID NO:81:

```
Ser  Leu  Val  Lys  Ala  Phe
1                   5
```

( 2 ) INFORMATION FOR SEQ ID NO:82:

( i ) SEQUENCE CHARACTERISTICS:
     ( A ) LENGTH: 6 amino acids
     ( B ) TYPE: amino acid
     ( D ) TOPOLOGY: linear ( x i ) SEQUENCE DESCRIPTION: SEQ ID NO:82:

```
Ser  Pro  Val  Lys  Ala  Phe
1                   5
```

( 2 ) INFORMATION FOR SEQ ID NO:83:

( i ) SEQUENCE CHARACTERISTICS:
     ( A ) LENGTH: 365 amino acids
     ( B ) TYPE: amino acid
     ( D ) TOPOLOGY: linear ( x i ) SEQUENCE DESCRIPTION: SEQ ID NO:83:

```
Ser  Lys  Thr  Cys  Tyr  Glu  Gly  Asn  Gly  His  Phe  Tyr  Arg  Gly  Lys  Ala
1              5                   10                       15

Ser  Thr  Asp  Thr  Met  Gly  Arg  Pro  Cys  Leu  Pro  Trp  Asn  Ser  Ala  Thr
               20                       25                       30

Val  Leu  Gln  Gln  Thr  Tyr  His  Ala  His  Arg  Ser  Asp  Ala  Leu  Gln  Leu
          35                       40                       45

Gly  Leu  Gly  Lys  His  Asn  Tyr  Cys  Arg  Asn  Pro  Asp  Asn  Arg  Arg  Arg
     50                       55                       60

Pro  Trp  Cys  Tyr  Val  Gln  Val  Gly  Leu  Lys  Pro  Leu  Val  Gln  Glu  Cys
65                       70                       75                       80

Met  Val  His  Asp  Cys  Ala  Asp  Gly  Lys  Lys  Pro  Ser  Ser  Pro  Pro  Glu
                85                       90                       95

Glu  Leu  Lys  Phe  Gln  Cys  Gly  Gln  Lys  Thr  Leu  Arg  Pro  Arg  Phe  Lys
               100                      105                      110

Ile  Ile  Gly  Gly  Glu  Phe  Thr  Thr  Ile  Glu  Asn  Gln  Pro  Trp  Phe  Ala
          115                      120                      125

Ala  Ile  Tyr  Arg  Arg  His  Arg  Gly  Gly  Ser  Val  Thr  Tyr  Val  Cys  Gly
     130                      135                      140

Gly  Ser  Leu  Ile  Ser  Pro  Cys  Trp  Val  Ile  Ser  Ala  Thr  His  Cys  Phe
145                      150                      155                      160

Ile  Asp  Tyr  Pro  Lys  Lys  Glu  Asp  Tyr  Ile  Val  Tyr  Leu  Gly  Arg  Ser
               165                      170                      175

Arg  Leu  Asn  Ser  Asn  Thr  Gln  Gly  Glu  Met  Lys  Phe  Glu  Val  Glu  Asn
          180                      185                      190

Leu  Ile  Leu  His  Lys  Asp  Tyr  Ser  Ala  Asp  Thr  Leu  Ala  His  His  Asn
     195                      200                      205

Asp  Ile  Ala  Leu  Leu  Lys  Ile  Arg  Ser  Lys  Glu  Gly  Arg  Cys  Ala  Gln
     210                      215                      220

Pro  Ser  Arg  Thr  Ile  Gln  Thr  Ile  Cys  Leu  Pro  Ser  Met  Tyr  Asn  Asp
225                      230                      235                      240
```

```
Pro Gln Phe Gly Thr Ser Cys Glu Ile Thr Gly Phe Gly Lys Glu Asn
            245                     250              255

Ser Thr Asp Tyr Leu Tyr Pro Glu Gln Leu Lys Met Thr Val Val Lys
            260                 265              270

Leu Ile Ser His Arg Glu Cys Gln Gln Pro His Tyr Tyr Gly Ser Glu
        275             280                 285

Val Thr Thr Lys Met Leu Cys Ala Ala Asp Pro Gln Trp Lys Thr Asp
    290             295                 300

Ser Cys Gln Gly Asp Ser Gly Gly Pro Leu Val Cys Ser Leu Gln Gly
305             310                 315                     320

Arg Met Thr Leu Thr Gly Ile Val Ser Trp Gly Arg Gly Cys Ala Leu
            325                 330                 335

Lys Asp Lys Pro Gly Val Tyr Thr Arg Val Ser His Phe Leu Pro Trp
            340             345                 350

Ile Arg Ser His Thr Lys Glu Glu Asn Gly Leu Ala Leu
        355             360             365
```